(12) United States Patent
Asano et al.

(10) Patent No.: US 12,029,724 B2
(45) Date of Patent: Jul. 9, 2024

(54) METHOD FOR INHIBITING TUMOR GROWTH

(71) Applicant: Eisai R&D Management Co., Ltd., Tokyo (JP)

(72) Inventors: Makoto Asano, Tsukuba (JP); Junji Matsui, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/090,360

(22) PCT Filed: Apr. 26, 2017

(86) PCT No.: PCT/JP2017/016633
§ 371 (c)(1),
(2) Date: Oct. 1, 2018

(87) PCT Pub. No.: WO2017/188350
PCT Pub. Date: Nov. 2, 2017

(65) Prior Publication Data
US 2019/0111022 A1   Apr. 18, 2019

(30) Foreign Application Priority Data
Apr. 28, 2016   (JP) .................................. 2016-091919

(51) Int. Cl.
*A61K 31/357* (2006.01)
*A61K 9/127* (2006.01)
*A61P 35/00* (2006.01)

(52) U.S. Cl.
CPC ............ *A61K 31/357* (2013.01); *A61K 9/127* (2013.01); *A61P 35/00* (2018.01)

(58) Field of Classification Search
CPC ........ A61K 31/357; A61K 9/127; A61P 35/00
See application file for complete search history.

(56) References Cited

U.S. PATENT DOCUMENTS

| | | | |
|---|---|---|---|
| 5,192,549 | A | 3/1993 | Barenolz et al. |
| 5,316,771 | A | 5/1994 | Barenolz et al. |
| 5,571,534 | A | 11/1996 | Jalonen et al. |

(Continued)

FOREIGN PATENT DOCUMENTS

| | | |
|---|---|---|
| CA | 2673924 | 7/2008 |
| CN | 101209243 | 7/2008 |

(Continued)

OTHER PUBLICATIONS

Yu, Y., et al in International Journal of Pharmaceutics, vol. 443, isses 1-2, Fe. 2013, pp. 9-16.*

(Continued)

*Primary Examiner* — Gollamudi S Kishore
(74) *Attorney, Agent, or Firm* — Fish & Richardson P.C.

(57) ABSTRACT

The present invention provides a method for inhibiting growth of at least one tumor selected from the group consisting of uterine cancer, esophageal cancer, pancreatic cancer, liver cancer, biliary tract cancer, duodenal cancer, lung cancer, kidney cancer, sarcoma, brain tumor, urothelial cancer, thyroid cancer, stomach cancer, and lymphoma in a patient, by administering to the patient a liposome composition comprising eribulin or a pharmaceutically acceptable salt thereof.

3 Claims, 4 Drawing Sheets

(56) References Cited

U.S. PATENT DOCUMENTS

| | | |
|---|---|---|
| 5,736,155 A | 4/1998 | Bally et al. |
| 5,759,573 A | 6/1998 | Kim |
| 5,821,349 A | 10/1998 | Djedaini-Pilard et al. |
| 6,051,251 A | 4/2000 | Zalipsky et al. |
| 6,214,865 B1 | 4/2001 | Littlefield et al. |
| 6,469,182 B1 | 10/2002 | Littlefield et al. |
| 6,653,341 B1 | 11/2003 | Littlefield et al. |
| 6,747,011 B1 | 6/2004 | Zhang |
| 7,488,802 B2 | 2/2009 | Collins et al. |
| 7,521,051 B2 | 4/2009 | Collins et al. |
| 7,982,060 B2 | 7/2011 | Austad et al. |
| 8,008,449 B2 | 8/2011 | Korman et al. |
| 8,093,410 B2 | 1/2012 | Chase et al. |
| 8,168,757 B2 | 5/2012 | Finnefrock et al. |
| 8,350,067 B2 | 1/2013 | Endo et al. |
| 8,354,509 B2 | 1/2013 | Carven et al. |
| 8,383,796 B2 | 2/2013 | Korman et al. |
| 9,968,583 B2 | 5/2018 | Kikuchi et al. |
| 10,945,990 B2 | 3/2021 | Matsui et al. |
| 11,071,713 B2 | 7/2021 | Kikuchi et al. |
| 11,083,705 B2 | 8/2021 | Semba et al. |
| 2002/0131995 A1* | 9/2002 | Szoka, Jr. ............ A61K 9/1271 424/450 |
| 2004/0156889 A1 | 8/2004 | Hu et al. |
| 2005/0118249 A1 | 6/2005 | Webb et al. |
| 2005/0118250 A1 | 6/2005 | Tardi et al. |
| 2006/0008909 A1 | 1/2006 | Cullis et al. |
| 2006/0104984 A1 | 5/2006 | Littlefield et al. |
| 2006/0147511 A1 | 7/2006 | Panzer et al. |
| 2007/0112176 A1 | 5/2007 | Seiki et al. |
| 2007/0116753 A1 | 5/2007 | Hong et al. |
| 2007/0155696 A1 | 7/2007 | Ishihara et al. |
| 2007/0244187 A1 | 10/2007 | Austad et al. |
| 2009/0196913 A1 | 8/2009 | Huang et al. |
| 2009/0196918 A1 | 8/2009 | Joguparthi et al. |
| 2010/0247629 A1 | 9/2010 | Gabizon et al. |
| 2011/0018419 A1 | 1/2011 | Suzuki et al. |
| 2011/0184190 A1 | 7/2011 | Endo et al. |
| 2011/0262524 A1 | 10/2011 | Bally et al. |
| 2011/0271358 A1 | 11/2011 | Freeman et al. |
| 2012/0058178 A1* | 3/2012 | Kikuchi ............... A61K 9/1271 424/450 |
| 2012/0128757 A1* | 5/2012 | Kikuchi ............... A61K 9/1271 424/450 |
| 2014/0044777 A1 | 2/2014 | Kikuchi et al. |
| 2014/0212479 A1* | 7/2014 | Zeinelden ............ A61K 9/127 424/450 |
| 2014/0248263 A1* | 9/2014 | Andersen ............. C07C 43/23 424/133.1 |
| 2015/0005343 A1 | 1/2015 | Nomoto et al. |
| 2015/0210769 A1 | 7/2015 | Freeman et al. |
| 2015/0246033 A1 | 9/2015 | Flynn et al. |
| 2016/0235671 A1 | 8/2016 | Li et al. |
| 2016/0296633 A1 | 10/2016 | Goldenberg et al. |
| 2016/0338954 A1* | 11/2016 | Brinker ............... A61K 31/7088 |
| 2017/0020817 A1* | 1/2017 | Singh ................... A61K 9/10 |
| 2017/0071903 A1 | 3/2017 | Funahashi et al. |
| 2018/0071247 A1 | 3/2018 | Matsui et al. |
| 2019/0010232 A1 | 1/2019 | Kalos et al. |
| 2019/0263927 A1 | 8/2019 | Olivo |
| 2021/0023047 A1 | 1/2021 | Semba et al. |
| 2021/0177802 A1 | 6/2021 | Semba et al. |
| 2022/0389110 A1 | 12/2022 | Jure-Kunkel et al. |

FOREIGN PATENT DOCUMENTS

| | | |
|---|---|---|
| CN | 103562406 | 2/2014 |
| CN | 105640935 | 6/2016 |
| CN | 107207580 | 9/2017 |
| EP | 1332755 | 8/2003 |
| EP | 1921086 | 5/2008 |
| EP | 2123260 | 11/2009 |
| EP | 2415464 | 2/2012 |
| JP | H07-501813 | 2/1995 |
| JP | H08-509230 | 10/1996 |
| JP | 2002-518384 | 6/2002 |
| JP | 2004-516247 | 6/2004 |
| JP | 2005-509000 | 4/2005 |
| JP | 2006-513189 | 4/2006 |
| JP | 2006-340714 | 12/2006 |
| JP | 2010-514708 | 5/2010 |
| JP | 5551683 | 5/2014 |
| JP | 2018-508516 | 3/2018 |
| RU | 2405601 | 12/2010 |
| RU | 2476216 C1 | 2/2013 |
| WO | WO 1993/011757 | 6/1993 |
| WO | WO 1994/023697 | 10/1994 |
| WO | WO 1999/065894 | 12/1999 |
| WO | WO 2002/032399 | 4/2002 |
| WO | WO 2003/041681 | 5/2003 |
| WO | WO 2004/004771 | 1/2004 |
| WO | WO 2004/056875 | 7/2004 |
| WO | WO 2004/058140 | 7/2004 |
| WO | WO 2004/072286 | 8/2004 |
| WO | WO 2005/046643 | 5/2005 |
| WO | WO 2005/118565 | 12/2005 |
| WO | WO 2006/037230 | 4/2006 |
| WO | WO 2007/026869 | 3/2007 |
| WO | WO 2007/061874 | 5/2007 |
| WO | WO 2008/080367 | 7/2008 |
| WO | WO 2008/156712 | 12/2008 |
| WO | WO 2010/027827 | 3/2010 |
| WO | WO 2010/077634 | 7/2010 |
| WO | WO 2010/113983 | 10/2010 |
| WO | WO 2010/113984 | 10/2010 |
| WO | WO 2011/066342 | 6/2011 |
| WO | WO 2011/094339 | 8/2011 |
| WO | WO 2012/119077 | 9/2012 |
| WO | WO 2012/135408 | 10/2012 |
| WO | WO 2013/019906 | 2/2013 |
| WO | WO 2014/087230 | 6/2014 |
| WO | WO 2014/159562 | 10/2014 |
| WO | WO 2014/193898 | 12/2014 |
| WO | WO 2014/199294 | 12/2014 |
| WO | WO 2014/208774 | 12/2014 |
| WO | WO 2015/112900 | 7/2015 |
| WO | WO 2015/134399 | 9/2015 |
| WO | WO 2015/134605 | 9/2015 |
| WO | WO 2015/183961 | 12/2015 |
| WO | WO 2015/184145 | 12/2015 |
| WO | WO 2016/130839 | 8/2016 |
| WO | WO 2016/141209 | 11/2017 |
| WO | WO 2017/188350 | 11/2017 |
| WO | WO 2018/071792 | 4/2018 |

OTHER PUBLICATIONS

Schoffiski et al in www.theLancet.com Oncology, vol. 12, Oct. 2011, pp. 1045-1052.*

Narayan, S., et al in Bioorganic & Medicinal Chemistry Letters, vol. 21, Issue 6, Mar. 2011, pp. 1639-1643.*

[No Author], "Ammonium Cations," The Illustrated Glossary of Organic Chemistry, [Retrieved on Mar. 9, 2016], retrieved from: URL<http://www.chem.ucla.edu/harding/IGOC/A/ammonium_cation.html>, 1 page.

[No Author], "Halaven Intravenour Injection 1mg," Package Insert for Halaven, Eisai, Ltd., Jul. 2011, 6 pages (with partial English Translation).

[No Author], "Novantron Infection 10mg, 20mg," Package Insert, ASKA Pharmaceutical Co., Ltd., Nov. 2011, 6 pages (with partial English Translation).

[No Author], WHO Drug Information, 2013, vol. 27, No. 1, pp. 68-69.

[No Author], WHO Drug Information, 2013, vol. 27, No. 2, pp. 161-162.

Adams et al., "Phase 2 study of pembrolizumab (pembro) monotherapy for previously treated metastatic triple-negative breast cancer (mTNBC): KEYNOTE-086 cohort A," Journal of Clinical Oncology, 2017, 35(15 suppl):1008.

Adams et al., "Phase 2 study of pembrolizumab as first-line therapy for PD-L1-positive metastatic triple-negative breast cancer (mTNBC):

(56) References Cited

OTHER PUBLICATIONS

Preliminary data from KEYNOTE-086 cohort B," Journal of Clinical Oncology, 2017, 35(15 suppl):1088.
Ahmadzadeh et al., "Tumor antigen-specific CD8 T cells infiltrating the tumor express high levels of PD-1 and are functionally impaired," Blood, 2009, 114(8):1537-1544.
Applicant Observation filed in Chinese Patent Application No. 201080014698.2, dated Apr. 2, 2013 to the first Chinese Office Action dated Oct. 24, 2012, 48 pages (with English Translation).
Arima et al., "Enhancement of antitumor effect of doxombicin by its complexation with γ-cyclodextrin in pegylated liposomes," Journal of Drug Targeting, 2006, 14(4):225-232.
Asano et al., "Broad-spectrum Preclinical Antitumor Activity of Eribulin (Halaven®): Combination with Anticancer Agents of Differing Mechanisms," Anticancer Research, 2018, 38:3375-3385.
Beijnen et al., "Aspects of the degradation kinetics of doxombicin in aqueous solution," International Journal of Pharmaceutics, Elsevier, 1986, 32:123-131.
Bolotin et al., "Ammonium sulfate gradients for efficient and stable remote loading of amphipathic weak bases into liposomes and ligandoliposomes," Journal of Liposome Research, 1994, 4(1):455-479, XP000572717.
Cardoso et al., "ESO-ESMO 2nd international consensus guidelines for advanced breast cancer (ABC2)," The Breast, 2014, 23:489-502.
ClinicalTrials.gov [online], "An open-label Multicenter Multiple Dose Phase 1 Study to Establish the Maximum Tolerated Dose of E7389 Liposomal Formulation in Patients With Solid Tumors," Apr. 2016, National Library of Medicine, Bethesda MD, USA,—NCT01945710, retrieved from: URL<https://clinicaltrials.gov/archive/NCT01945710/2016_04_19>, 6 pages.
ClinicalTrials.gov [online], "Study NCT01848834—Study of MK-3475 in Participants With Advanced Solid Tumors (MK-3475-012/KEYNOTE-012)," Apr. 2014, retrieved from: URL<https://clinicaltrials.gov/ct2/history/NCT01848834?V_24=View>, 7 pages.
Coates et al., "Tailoring therapies—improving the management of early breast cancer: St Gallen International Expert Consensus on the Primary Therapy of Early Breast Cancer 2015," Annals of Oncology, 2015, 26(8):1533-1546.
Communication under Rule 71(3) EPC in European Patent Application No. 10758754.5, dated Jan. 19, 2017, 54 pages.
Communication under Rule 71(3) EPC in European Patent Application No. 10758755.2, dated Feb. 25, 2016, 7 pages.
Completion of Final Requirements in Philippine Patent Application No. 1-2011-501838, dated Aug. 27, 2015, 1 page.
Cortes et al., "Eribulin monotherapy versus treatment of physician's choice in patients with metastatic breast cancer (EMBRACE): a phase 3 open-label randomised study," Lancet, 2011, 377:914-923.
CTEP Rapid Communication, "Solicitation for Letters of Intent: Clinical trials—Preclinical experiments, E7389, Halichondrin B analog (NSC 707389)," 11 pages.
Cullis et al., "pH Gradients and Membrane Transport in liposomal Systems," Trends in Biotechnology, 1991, 9(8)268-272.
Danhier et al., "Strategies to improve the EPR effect for the delivery of anti-cancer nanomedicines," Cancer Cell & Microenvironment, 2015, 2:e808.
Decision on Grant in Russian Application No. 2011139715, dated Sep. 25, 2012, 14 pages (with English Translation).
Decision to Grant in Japanese Patent Application No. 2011-507239, dated Aug. 27, 2014, 5 pages (with English Translation).
Decision to Grant in Japanese Patent Application No. 2011-507240, dated May 7, 2014, 5 pages (with English Translation).
Decision to Grant in Japanese Patent Application No. 2014-092382, dated Jun. 2, 2015, 6 pages (with English Translation).
DesJardins et al., "A high-performance liquid chromatography-tandem mass spectrometry method for the clinical combination study of carboplatin and anti-tumor agent eribulin mesylate (E7389) in human plasma," Journal of Chromatography B, 2008, 875:373-382.
Devriese et al., "Eribulin mesylate pharmacokinetics in patients with solid tumors receiving repeated oral ketoconazole," Invest New Drugs, 2013, 31:381-389.
Dong et al., "Tumor-associated B7-H1 promotes T-cell apoptosis: A potential mechanism of immune evasion," Natural Medicine, 2002, 8(8):793-800.
Dos Santos et al., "pH gradient loading of anthracyclines into cholesterol-free liposomes: enhancing drug loading rates through use of ethanol," Biochimica et Biophysica Acta, 2004, 1661:47-60.
Drummond, et al., Optimizing Liposomes for Delivery of Chemotherapeutic Agents to Solid Tumors, Pharmacological Reviews, 1999, 51(4):691-743.
Dybdal-Hargreaves et al., "Eribulin Mesylate: Mechanism of Action of a Unique Microtubule-Targeting Agent," Clinical Cancer Research, 2015, 21(11):2445-2452.
Eisai Co., Ltd., "FY2011 Financial Results Presentation," May 15, 2012, 68 pages (with English Translation).
Eisai Co., Ltd., "Halaven®," Code DI-T-HAL107, 6th edition, Feb. 2016, pp. 1-6 (with English Translation).
Eisai Co., Ltd., "Material Safety Data Sheet for Eribulin Mesylate," Oct. 2009, prepared by Greg Baker, 6 pages.
Eisai Co., Ltd., Eisai Public Relations Department, "Eisai and Merck Enter Collaboration to Explore Novel Combination Regimens of Anti-PD-1 Therapy with Multi-targeting RTK Inhibitor and Microtubule Dynamics in Multiple Types of Cancer," Mar. 4, 2015, retrieved from: URL<http//www.eisai.com/news/news201518.html>, 8 pages.
Eisai Co., Ltd., News Release No. 19-72, "Eisai to Present Abstracts on Oncology Products and Pipeline at ESMO 2019 Congress," dated Sep. 24, 2019, 3 pages.
Examiner's Answer in United States U.S. Appl. No. 14/061,426 dated Feb. 28, 2020, 3 pages.
Excerpted file history of U.S. Appl. No. 13/260,864: Issue fee payment (dated Apr. 9, 2018); Supplemental Notice of Allowability (dated Jan. 24, 2018); Corrected Filing Receipt (dated Jan. 17, 2018); Notice of Allowance and Issue Fee Due (dated Jan. 8, 2018).
Extended European Search Report in European Patent Application No. 10758754.5 dated Oct. 8, 2012, 10 pages.
Extended European Search Report in European Patent Application No. 10758755.2, dated Oct. 31, 2012 with corrected Written Opinion for EESR dated Dec. 19, 2012, 24 pages.
Extended European Search Report in European Patent Application No. 17789632.1, dated Nov. 27, 2019, 9 pages.
Fatouros et al., "Liposomes encapsulating prednisolone and prednisolone-cyclodextrin complexes: comparison of membrane integrity and drug release," European Journal of Pharmaceutical Sciences, 2001, 13:287-296.
Fenske et al., "Entrapment of small molecules and nucleic acid-based drugs in liposomes," Methods in Enzymology, 2005, 391:7-40.
Final and Non Final Office actions in United States Patent Application No. 13/260.864, dated Nov. 10, 2015 and Oct. 14, 2015 respectively, 20 pages.
Final Rejection in Algerian Patent Application No. 110640, dated Aug. 18, 2013, 2 pages (with English Translation).
FormuMax Scientific Inc., "Doxoves-Liposome Doxorubicin Compared to Doxil," Doxoves-Liposomal Doxorubicin, 1995, 1-4, XP002684032, [Retrieved on Sep. 24, 2012], retrieved from: URL <www.liposomeexpert.com/categories/Drug-Loaded-Liposomes>.
Gao et al., "Overexpression of PD-L1 Significantly Associates with Tumor Aggressiveness and Postoperative Recurrence in Human Hepatocellular Carcinoma," Clin. Cancer Res., 2009, 15(3):971-979.
Ghebeh et al. "FOXP3* $T_{regs}$ and B7-HI+/PD-1+ T lymphocytes co-infiltrate the tumor tissues of high-risk breast cancer patients: Implication for immunotherapy," BMC Cancer, 2008, 8:57.
Ghebeh et al., "The B7-H1 (PD-L1) T Lymphocyte-Inhibitory Molecule is Expressed in Breast Cancer Patients with Infiltrating Ductal Carcinoma: Correlation with Important High-Risk Prognostic Factors," Neoplasia, 2006, 8(3):190-198.
Golub et al., "Molecular Classification of Cancer: Class Discovery and Class Prediction by Gene Expression Monitoring," Science, 1999, 286:531-537.

(56) References Cited

OTHER PUBLICATIONS

Hagiwara et al., "Preparation and pharmaceutical evaluation of liposomes entrapping salicylic acid/γ-cyclodextrin conjugate," Chem. Pharm. Bull., 2006, 54(1):26-32.
Hamanishi et al., "Programmed cell death 1 ligand 1 and tumor-infiltrating CD8+ T lymphocytes are prognostic factors of human ovarian cancer," PNAS, 2007, 104(9):3360-3365.
Haran et al., "Transmembrane ammonium sulfate gradients in liposomes produce efficient and stable entrapment of amphipathic weak bases," Biochimica et Biophysica Acta. Biomembranes, 1993, 1151(2):201-215.
Hart et al., "Acid-catalyzed reactions of homohalichondrin B, a marine sponge-derived antitumor polyether macrolide," The Journal of Organic Chemistry, 1996, 61(8):2888-2890.
Hearing Notice in Indian Patent Application No. 6850/DELNP/2011, dated Aug. 17, 2017, 3 pages.
Hino et al., "Tumor Cell Expression of Programmed Cell Death-1 Ligand 1 Is a Prognostic Factor for Malignant Melanoma," Cancer, 2010, 116(7):1757-1766.
Inman et al., "PD-L1 (B7-H1) Expression by Urothelial Carcinoma of the Bladder and BCG-Induced Granulomata," Cancer, 2007, 109(8):1499-1505.
International Preliminary Report on Patentability in International Application No. PCT/US2016/020734, dated Sep. 5, 2017, 9 pages.
International Preliminary Report on Patentability in International Application No. PCT/US2017/056552, dated Apr. 25, 2019, 8 pages.
International Preliminary Report on Patentability in International Patent Application No. PCT/JP2017/016633, dated Oct. 30, 2018, 22 pages (with English Translation).
International Preliminary Report on Patentability in International Patent Application No. PCT/JP2010/055769, dated Oct. 4, 2011, 11 pages (with English Translation).
International Preliminary Report on Patentability in International Patent Application No. PCT/JP2010/055770, dated Nov. 15, 2011, 9 pages (with English Translation).
International Search Report and Written Opinion in International Patent Application No. PCT/US2017/056552, dated Jan. 2, 2018, 11 pages.
International Search Report in International Application No. PCT/JP2010/055770, dated Jun. 1, 2010, 2 pages.
International Search Report in International Application No. PCT/US2016/020734, dated Apr. 28, 2016, 7 pages.
International Search Report in International Patent Application No. PCT/JP2010/0055769, dated Jun. 8, 2010, 5 pages (with English Translation).
International Search Report in International Patent Application No. PCT/JP2017/016633, dated Jun. 6, 2017, 6 pages (with English Translation).
International Search Report in International Patent Application No. PCT/JP2018/020456, dated Aug. 28, 2018, 5 pages (with English Translation).
Intimation Notification in Indian Patent Application No. 6850/DELNP/2011, dated Aug. 23, 2018, 1 page.
Ishida et al., "Targeted delivery and triggered release of liposomal doxorubicin enhances cytotoxicity against human B lymphoma cell," Biochimica et Biophysica Acta, 2001, 1515:144-158.
IUPAC Goldbook, "Onium Compunds," Entry, [Retrieved on Mar. 9, 2016], retrieved from: URL<http://goldbook.iupac.org/O04291.html>, 2 pages.
Jordan et al., "The primary antimitotic mechanism of action of the synthetic halichondrin E7389 is suppression of microtubule growth," Molecular Cancer Therapeutics, 2005, 4(7):1086-1095.
Kazmi et al., "Real-world 1-year survival analysis of patients with metastatic breast cancer with liver or lung visceral metastasis treated with eribulin, gemcitabine," Poster Display, Abstract No. 366P, displayed Sep. 29, 2019, European Society for Medical Oncology (ESMO) 2019 Congress, Barcelona, Spain, 1 page.
Kikuchi, et al. "Liposome I—Method of Preparing and Testing," Cell Engineering, 1983, 2(9):1136-1149 (with English Translation).

Kim et al., "Multivescular liposomes containing cytarabine entrapped in the presence of hydrochloric acid for intracavitary chemotherapy," Cancer Treatment Reports, 1987, 71(7-8):705-711.
Kim et al., "Preparation of multivesicular liposomes," Biochimica et Biophysica Acta, 1983, 728:339-348.
Knollman et al., "Muscle-invasive urothelial bladder cancer: an update on systemic therapy," Therapeutic Advances In Urology, 2015, 7(6):312-330.
Kuznetsov et al., "Antiproliferative effects of halichondrin B analog eribulin mesylate (E7389) against paclitaxel-resistant human cancer cells in vitro," AACR-NCI-EORTC International Conference: Molecular Targets and Cancer Therapeutics. Abstract C58. Oct. 2007, 2 pages.
Lasic et al., "Gelation of liposome interior; A novel method for drug encapsulation," FEBS Lett., 1992, 312(2-3):255-258.
Lasic et al., "Transmembrane gradient driven phase transitions within vesicles: lessons for drug delivery," Biochimica et Biophysica Acta., 1995, 1239(2):145-156.
Liposomes, ed. Fude, CUI, Fifth Edition, People's Press of Hygiene, Mar. 2004, p. 386-394 (English explanation on Chinese Office Action in CN Appln. No. 201080014698.2 dated Oct. 24, 2012), 8 pages.
Loftsson T et al.: "Solubilization and Stabilization of Drugs Through Cyclodextrin Complexation", Acta Pharmaceutica Nordica, 1991, 3(4):215-217.
Maeda, "EPR Effect," Kobunshi, 2000, 49(3):129 (with English Translation).
Maestrelli et al., "Effect of preparation technique on the properties of liposomes encapsulating ketoprofen-cyclodextrin complexes aimed for transdermal delivery," International Journal of Pharmaceutics, 2006, 312:53-60.
Matsumura et al., "A new concept for macromolecular therapeutics in cancer chemotherapy: mechanism of tumoritropic accumulation of proteins and the antitumor agent smancs," Cancer Research, 1986, 46:6387-6392.
Maurer-Spurej et al., "Factors influencing uptake and retention of amino-containing drugs in large unilamellar vesicles exhibiting transmembrane pH gradients," Biochimica et Biophysica Acta, 1999. 1416:1-10.
Mayer et al., "Uptake of adriamycin into large unilamellar vesicles in response to a pH gradient," Biochimica et Biophysica Acta, 1986, 857:123-126.
Memorandum in Response to Official Action in Israeli Patent Application No. 215059, dated Dec. 2, 2014, 58 pages.
Merck Sharp & Dohme Corp., "Highlights of Prescribing Information—Keytruda® (pembrolizumab)," Label, Suppl. 8, revised Oct. 2016, FDA Ref. ID: 4003165, retrieved from: URL<https://www.accessdata.fda.gov/drugsatfda_docs/label/2016/125514s008s012lbl.pdf>, 29 pages.
Merck Sharp & Dohme Corp., "Highlights of Prescribing Information—Keytruda® (pembrolizumab)," Label, Suppl. 9, revised Aug. 2016, FDA Ref. ID: 3968676, retrieved from: URL<https://www.accessdata.fda.gov/drugsatfdadocs/labeF2016/125514s0091bl.pdf>, 26 pages.
Nakanishi et al., "Overexpression of B7-H1 (PD-L1) significantly associates with tumor grade and postoperative prognosis in human urothelial cancers," Cancer Immunol. Immunother., 2007, 56:1173-1182.
Nanda et al., "Pembrolizumab in Patients With Advanced Triple-Negative Breast Cancer: Phase 1b KEYNOTE-012 Study," Journal of Clinical Oncology, 2016, 34(21):2460-2467.
Nanda, "Pembrolizumab Shows Potential in Breast Cancer," Cancer Discovery, 2015, 5(2):100-101.
Narayan et al. "Novel second generation analogs of eribulin. Part III: blood-brain barrier permeability and in vivo activity in a brain tumor model," Bioorganic & Medicinal Chemistry Letters, 2011, 21(6):1639-1643.
Nippon Kayaku Co., Ltd., "Adriacin® for injection 10—Adriacin® for injection 50," Package Insert, revised Aug. 2011, 6 pages (with English Translation).
Nippon Kayaku Co., Ltd., "Exal® for injection 10 mg—Japanese Pharmacopeia (JP) Vinblastine Sulfate for Injection," Package Insert, revised Jul. 2011, 7 pages (with Partial Translation).

(56) References Cited

OTHER PUBLICATIONS

Nippon Kayaku Co., Ltd., "Oncovin® for injection 1 mg—Vincristine Sulfate Preparation," Package Insert, revised Aug. 2009, 7 pages (with Partial Translation).
Nippon Kayaku Co., Ltd., "Rozeus® Intravenous Solution 10 mg—Rozeus® Intravenous Solution 40 mg—Vinorelbine Ditartrate Intravenous Solution," Package Insert, revised Nov. 2009, 5 pages (with Partial Translation).
Nomi et al., "Clinical Significance and Therapeutic Potential of the Programmed Death-1 Ligand/Programmed Death-1 Pathway in Human Pancreatic Cancer," Clin. Cancer Res., 2007, 13(7):2151-2157.
Notice of Allowance in Australian Patent Application No. 2014200717, dated Feb. 13, 2016, 2 pages.
Notice of Allowance in Canadian Patent Application No. 2756811, dated Feb. 10, 2014, 1 page.
Notice of Allowance in Chilean Patent Application No. 2444-2011, dated Jul. 3, 2018, 8 pages (with English Translation).
Notice of Allowance in Chinese Patent Application No. 201080014698.2, dated Aug. 6, 2014, 4 pages (with English Translation).
Notice of Allowance in Colombian Patent Application No. 11-130828, dated Jan. 21, 2014, 12 pages (with English Translation).
Notice of Allowance in Indonesian Patent Application No. W00201103470 dated Apr. 20, 2017, 4 pages (with English Translation.
Notice of Allowance in Israeli Patent Application No. 215059, dated Nov. 25, 2015, 3 pages (with English Translation).
Notice of Allowance in Korean Patent Application No. 10-2011-7022860, dated Jan. 9, 2015, 4 pages (with English Translation).
Notice of Allowance in Mexican Patent Application No. MX/A/2011/009632, dated Oct. 14, 2014, 2 pages (with English Translation).
Notice of Allowance in New Zealand Patent Application No. 595212, dated Feb. 25, 2014, 1 page.
Notice of Allowance in Taiwanese Patent Application No. 099109838, dated Jan. 23, 2013, 5 pages (with English Translation).
Notice of Allowance in Ukrainian Patent Application No. a201111426, dated Jul. 23, 2013, 7 pages (with English Translation).
Notice of Final Rejection in Korean Patent Application No. 10-2011-7022860, dated Sep. 23, 2014, 5 pages (with English Translation).
Notice of Panel Decision in U.S. Appl. No. 14/061,426, dated Oct. 1, 2019, 2 pages.
Notice of Reason for Rejection in Japanese Patent Application No. 2011-507239, dated Feb. 27, 2014, 6 pages (with English Translation).
Notice of Reason for Rejection in Japanese Patent Application No. 2011-507240, dated Feb. 6, 2014, 7 pages (with English Translation).
Notice of Reason for Rejection in Japanese Patent Application No. 2014-092382, dated Jan. 28, 2015, 5 pages (with English Translation).
Notification of the Brazilian Patent and Trademark Office and Documents forwarded by ANVISA (Brazilian Health Surveillance Agency) for Brazilian Patent Application No. PI1014527-3, including transmittal letter (dated Jul. 31, 2019); Technical Written Opinion of Consent of a Patent Application of Pharmaceutical products and Processes (dated Jul. 18, 2019), supporting documents (dated Jul. 24, 2019), and "Documents Forwarded by ANVIA" (Sep. 5, 2019).
Observation Notification in Peruvian Patent Application No. 001798-2015, dated Feb. 12, 2020, 11 pages (with English Translation).
Observation Notification in Peruvian Patent Application No. 001798-2015, dated Oct. 16, 2019, 15 pages (with English Translation).
Office Action in Australian Patent Application No. 2010232347, dated May 11, 2012, 2 pages.
Office Action in Australian Patent Application No. 2014200717, dated Aug. 14, 2015, 2 pages.
Office Action in Brazilian Patent Application No. PI10145273, dated Mar. 30, 2020, 24 pages (with English Translation).

Office Action in Canadian Patent Application No. 2756811, dated Dec. 19, 2012, 4 pages.
Office Action in Canadian Patent Application No. 2756811, dated Jul. 17, 2013, 2 pages.
Office Action in Chilean Patent Application No. 2444-2011, dated Jan. 16, 2014, 6 pages (with English Translation).
Office Action in Chilean Patent Application No. 2444-2011, dated Jan. 21, 2015, 20 pages (with English Translation).
Office Action in Chilean Patent Application No. 2444-2011, dated Jul. 11, 2013, 19 pages (with English Translation).
Office Action in Chilean Patent Application No. 2444-2011, dated Dec. 18, 2015, 15 pages (with English Translation).
Office Action in Chinese Patent Application No. 201080014698.2 dated Oct. 24, 2012, 14 pages (with English Translation).
Office Action in Chinese Patent Application No. 201080014698.2, dated Aug. 8, 2013, 12 pages (with English Translation).
Office Action in Chinese Patent Application No. 201080014698.2, dated Mar. 28, 2014, 6 pages (with English Translation).
Office Action in Chinese Patent Application No. 201680025588.3, dated Jan. 6, 2020, 28 pages (with English Translation).
Office Action in Colombian Patent Application No. 11-130828, dated Aug. 8, 2013, 30 pages (with English Translation).
Office Action in Egyptian Patent Application No. PCT1637/2011, dated Jan. 14, 2016, 10 pages (with English Translation).
Office Action in European Patent Application No. 10758754.5, dated Jan. 24, 2014, 7 pages.
Office Action in European Patent Application No. 10758755.2, dated Jan. 24, 2014, 4 pages.
Office Action in European Patent Application No. 16710891.9, dated Aug. 13, 2019, 6 pages.
Office Action in European Patent Application No. 16710891.9, dated Mar. 31, 2020, 6 pages.
Office Action in Indian Patent Application No. 201747034283, dated Feb. 28, 2020, 7 pages (with English Translation).
Office Action in Indian Patent Application No. 6850DELNP2011, dated Nov. 10, 2016, 9 pages.
Office Action in Indonesian Patent Application No. W0020113470, dated Nov. 29, 2013, 7 pages (with English Translation).
Office Action in Israeli Patent Application No. 215059, dated Aug. 4, 2014, 3 pages (with English Translation).
Office Action in Japanese Patent Application No. 2017-546075, dated Jan. 7, 2020, 6 pages (with English Translation).
Office Action in Korean Patent Application No. 10-2011-7022860, dated Jul. 22, 2013, 20 pages (with English Translation).
Office Action in Korean Patent Application No. 10-2011-7022860, dated May 20, 2014, 11 pages (with English Translation).
Office Action in Korean Patent Application No. 10-2011-7022860, Notice of Preliminary Rejection, dated Dec. 28, 2012, 7 pages (with English Translation).
Office Action in Malaysian Patent Application No. PI2011004382, dated Apr. 15, 2013, 3 pages.
Office Action in Malaysian Patent Application No. PI2011004382, dated Sep. 30, 2016, 2 pages.
Office Action in Mexican Patent Application No. MX/a/2011/009632, dated Apr. 22, 2013, 12 pages (with English Translation).
Office Action in Mexican Patent Application No. MX/a/2011/009632, dated Aug. 7, 2012, 6 pages (with English Translation).
Office Action in Mexican Patent Application No. MX/a/2011/009632, dated Jan. 17, 2014, 6 pages (with English Translation).
Office Action in New Zealand Patent Application No. 595212, dated Aug. 14, 2012, 1 page.
Office Action in Peruvian Patent Application No. 001735-2011/DIN, dated Jan. 9, 2014, 2 pages (with English Translation).
Office Action in Peruvian Patent Application No. 001735-2011/DIN, dated Nov. 23, 2012, 15 pages (with English Translation).
Office Action in Peruvian Patent Application No. 001735-2011/DIN, dated Sep. 29, 2014, 7 pages (with English Translation).
Office Action in Philippine Patent Application No. Jan. 2011/501838, dated Jun. 4, 2015, 1 page.
Office Action in Philippine Patent Application No. 12011-501838, dated Sep. 17, 2014, 2 pages.
Office Action in Philippine Patent Application No. 1-2011-501838, dated Aug. 8, 2013, 1 page.

(56) References Cited

OTHER PUBLICATIONS

Office Action in Russian Patent Application No. 2017132877, dated Aug. 29, 2019, 12 pages (with English Translation).
Office Action in Russian Patent Application No. 2017132877, dated Jan. 27, 2020, 8 pages (with English Translation).
Office Action in Russian Patent Application. No. 2011139715/20(059371), dated Nov. 28, 2011, (with partial English Translation), with Applicant Response filed on Jan. 30, 2012, 4 pages.
Office Action in Taiwanese Patent Application No. 099109838, dated Jun. 22, 2012, 9 pages (with English Translation).
Office Action in U.S. Appl. No. 13/260,864, dated Feb. 3, 2017, 11 pages.
Office Action in U.S. Appl. No. 13/260,864, dated Jul. 13, 2015, 11 pages.
Office Action in U.S. Appl. No. 13/260,864, dated Jun. 27, 2016, 10 pages.
Office Action in U.S. Appl. No. 13/260,864, dated Mar. 10, 2014, 8 pages.
Office Action in U.S. Appl. No. 13/260,864, dated Sep. 26, 2014, 15 pages.
Office Action in U.S. Appl. No. 13/260,872, dated Apr. 24, 2013, 24 pages.
Office Action in U.S. Appl. No. 13/260,872, dated Aug. 1, 2012, 17 pages.
Office Action in U.S. Appl. No. 14/061,426 dated Oct. 30, 2017, 17 pages.
Office Action in U.S. Appl. No. 14/061,426, dated May 30, 2019, 17 pages.
Office Action in U.S. Appl. No. 14/061,426, dated May 31, 2017, 39 pages.
Office Action in U.S. Appl. No. 14/061,426, dated Nov. 19, 2018, 23 pages.
Office Action in U.S. Appl. No. 14/061,426, dated Sep. 24, 2015, 17 pages.
Office Action in U.S. Appl. No. 14/061,426, dated Mar. 18, 2016, 24 pages.
Office Action in U.S. Appl. No. 15/554,540, dated Jan. 2, 2020, 15 pages.
Office Action in U.S. Appl. No. 15/554,540, dated Mar. 22, 2020, 27 pages.
Office Action in U.S. Appl. No. 16/835,719, dated Jun. 29. 2020, 15 pages.
Office Action in Vietnamese Patent Application No. 1-2011-02950, dated Aug. 16, 2013, 3 pages (with English Translation).
Office Action in Vietnamese Patent Application No. 1-2011-02950, dated Mar. 31, 2016, 3 pages (with English Translation).
Official Decision in Egyptian Patent Application No. PCT1637/2011, dated Jan. 3, 2017, 8 pages (with English Translation).
Official Notification in Peruvian Patent Application No. 001735-2011/DIN, dated Jul. 16, 2015, 28 pages (with English Translation).
Official Notification in Vietnamese Patent Application No. 1-2011-02950, dated Jan. 24, 2017, 2 pages (with English Translation).
Ohigashi et al., "Clinical Significance of Programmed Death-1 Ligand-1 and Programmed Death-1 Ligand-2 Expression in Human Esophageal Cancer," Clin. Cancer Res., 2005, 11(8):2947-2953.
Okouneva et al., "Inhibition of centromere dynamics by eribulin (E7389) during mitotic metaphase," Molecular Cancer Therapeutics, 2008, 7(7):2003-2011.
Opposition in Colombian Patent Application No. 11-130828, dated Apr. 30, 2012, 14 pages (with English Translation).
Opposition in Colombian Patent Application No. 11-130828, dated Jul. 25, 2012, 14 pages (with English Translation).
Opposition in Peruvian Patent Application No. 001735-2011/DIN, dated Jan. 20, 2015, 25 pages (with English Translation).
Opposition in Peruvian Patent Application No. 001798-2015, dated Jan. 25, 2016, 18 pages (with English Translation).
Pardoll, "The blockade of immune checkpoints in cancer immunotherapy," Nature Reviews Cancer, 2012, 12:252-264.
Peleg-Shulman et al., "Characterization of sterically stabilized cisplatin liposomes by nuclear magnetic resonance," Biochimica et Biophysica, 2001, 1510(1-2): 278-291.
Petition in Japanese Patent Application No. 2014-092382, dated Dec. 26, 2014, 9 pages (with English Translation).
Piel et al., "Betamethasone-in-cyclodextrin-in-liposome: The effect of cyclodextrins on encapsulation efficiency and release kinetics," International Journal of Pharmaceutics, 2006, 312:75-82.
Poujol et al., "Stability of the ready-to use solutions of eribulin for intravenous infusion," Annales pharmaceutiques françaises, 2012, 70(5):249-255.
Preliminary Amendment filed in Japanese Patent Application No. 2014-092382 dated May 28, 2014, 4 pages (with English Translation).
Preliminary Conclusion in Ukrainian Patent Application No. a201111426, dated Apr. 8, 2013, 8 pages (with English Translation).
Rajora et al., "Impact of the Enhanced Permeability and Retention (EPR) Effect and Cathepsins Levels on the Activity of Polymer-Drug Conjugates," Polymers, 2014, 6:2186-2220.
Resolution in Peruvian Patent Application No. 001735-2011/DIN, dated Nov. 30, 2015, 50 pages (with English Translation).
Response filed in Algerian Patent Application No. 110640, dated Aug. 29, 2016, 26 pages (with English Translation).
Response filed in Australian Patent Application No. 2014200717, dated Dec. 22, 2015, 7 pages.
Response filed in Canadian Patent Application No. 2756811, dated Jan. 16, 2014, 15 pages.
Response filed in Canadian Patent Application No. 2756811, dated Jun. 19, 2013 to the Office Action dated Dec. 19, 2012, 21 pages.
Response filed in Chilean Patent Application No. 2444-2011, dated Apr. 16, 2015 to the Office Action dated Jan. 21, 2015, 142 pages (with English Translation).
Response filed in Chilean Patent Application No. 2444-2011, dated Jun. 5, 2015, 8 pages (with English Translation).
Response filed in Chilean Patent Application No. 2444-2011, dated Mar. 11, 2014 to the Opposition dated Jan. 2014, 6 pages (with English Translation).
Response filed in Chilean Patent Application No. 2444-2011, dated Mar. 14, 2016 to the Office Action dated Dec. 11, 2015, 12 pages (with English Translation).
Response filed in Chinese Patent Application No. 201080014698.2, dated Dec. 23, 2013 to Office Action dated Aug. 8, 2013, 14 pages (with English Translation).
Response filed in Chinese Patent Application No. 201080014698.2, dated May 29, 2014 to the Office Action dated Mar. 28, 2014, 13 pages (with English Translation).
Response filed in Colombian Patent Application No. 11-130828, dated Dec. 2, 2013, 24 pages (with English Translation).
Response filed in Colombian Patent Application No. 11-130828, dated Jan. 14, 2013 to the Opposition dated Jul. 25, 2012, 10 pages (with English Translation).
Response filed in Egyptian Patent Application No. PCT1637/2011, dated Apr. 18, 2016, 20 pages (with English Translation).
Response filed in Egyptian Patent Application No. PCT1637/2011, dated Mar. 30, 2017, to the Office Decision dated Jan. 3, 2017, 21 pages (with English Translation).
Response filed in European Patent Application No. 10758754.5, dated Aug. 1, 2014 to Communication to Art 94(3) dated Jan. 24, 2014, 15 pages.
Response filed in European Patent Application No. 10758754.5, dated May 3, 2013 to the Office Action dated Oct. 25, 2012 and to the EESR issued on Oct. 8, 2012, 8 pages.
Response filed in European Patent Application No. 10758755.2, dated Jun. 3, 2014 to the Office Action dated Jan. 24, 2014, 82 pages.
Response filed in European Patent Application No. 10758755.5, dated May 29, 2013 to the EESR issued on Nov. 19, 2012, 10 pages.
Response filed in European Patent Application No. 17789632.1, dated Jun. 24, 2020, to the Communication Pursuant to Rules 70(2)/70a(2) EPC dated Dec. 17, 2019, including Amendment, 5 pages.

(56) References Cited

OTHER PUBLICATIONS

Response filed in Indian Patent Application No. 6850/DELNP/2011, dated Oct. 3, 2017 to Result for Hearing Notice, including Amendment, 320 pages.
Response filed in Indonesian Patent Application No. W00201103470, dated Mar. 25, 2014, 7 pages (with English Translation).
Response filed in Japanese Patent Application No. 2011-507239, dated Apr. 28, 2014 to the Office Action dated Feb. 27, 2014, 5 pages (with English Translation).
Response filed in Japanese Patent Application No. 2011-507240, dated Apr. 7, 2014 to the Office Action dated Feb. 6, 2014, 26 pages (with English Translation).
Response filed in Japanese Patent Application No. 2014-092382, dated Mar. 27, 2015 to the Office Action dated Jan. 28, 2015, including Amendment and argument, 13 pages (with English Translation).
Response filed in Korean Patent Application No. 10-2011-7022860, dated Dec. 24, 2014 to the Notice of Final Rejection dated Sep. 23, 2014, 18 pages (with English Translation).
Response filed in Korean Patent Application No. 10-2011-7022860, dated Feb. 28, 2013 to the Office Action dated Dec. 28, 2012, 31 pages (with English Translation).
Response filed in Korean Patent Application No. 10-2011-7022860, dated Jan. 22, 2014 to the Office Action dated Jul. 22, 2013, 31 pages (with English Translation).
Response filed in Korean Patent Application No. 10-2011-7022860, dated Jul. 18, 2014 to the Office Action dated May 20, 2014, including amendment, 15 pages (with English Translation).
Response filed in Malaysian Patent Application No. PI2011004382, dated Jun. 14, 2013 to Substantive Examination Adverse Report dated Apr. 15, 2013, 6 pages.
Response filed in Mexican Patent Application No. MX/a/2011/009632 dated Jan. 7, 2013, to the Office Action dated Aug. 7, 2012, 17 pages (with English Translation).
Response filed in Mexican Patent Application No. MX/a/2011/009632, dated Jun. 17, 2014, 22 pages (with English Translation).
Response filed in Mexican Patent Application No. MX/a/2011/009632, dated Sep. 18, 2013 to the Office Action dated Apr. 22, 2013, 20 pages (with English Translation).
Response filed in New Zealand Patent Application No. 595212, dated Feb. 7, 2014, 4 pages.
Response filed in Peruvian Patent Application No. 001735-2011/DIN, dated Aug. 12, 2015 18 pages (with English Translation).
Response filed in Peruvian Patent Application No. 001735-2011/DIN, dated Jan. 20, 2014, 2 pages (with English Translation).
Response filed in Peruvian Patent Application No. 001735-2011/DIN, dated Jan. 21, 2013 to the Peruvian Opposition issued Nov. 23, 2012, 5 pages (with English Translation).
Response filed in Peruvian Patent Application No. 001735-2011/DIN, dated May 20, 2015, 48 pages (with English Translation).
Response filed in Peruvian Patent Application No. 001735-2011/DIN, dated Oct. 27, 2014 to Office Action dated Sep. 29, 2014, 3 pages.
Response filed in Peruvian Patent Application No. 001798-2015, dated Jan. 4, 2020 to the Observation, 12 pages (with English Translation).
Response filed in Peruvian Patent Application No. 1798-2015, dated Apr. 28, 2016, 10 pages (with English Translation).
Response filed in Philippine Patent Application No. 1-2011-501838, dated Jul. 24, 2015, 13 pages.
Response filed in Philippine Patent Application No. 1-2011-501838, dated Nov. 11, 2014, submitting English translation of JP 5551683 B2 in reply to Paper No. 9 mailed Sep. 17, 2014, 59 pages.
Response filed in Philippine Patent Application No. 1-2011-501838, dated Sep. 18, 2015 to the Office Action dated Aug. 27, 2015, 1 page.
Response filed in Philippine Patent Application No. 1-2011-501838, dated Sep. 30, 2013 to the Office Action dated Aug. 8, 2013, 1 page.
Response filed in Russian Patent Application No. 2011139715/20(059371), dated Jan. 30, 2012, 12 pages (with partial English Translation).
Response filed in Ukrainian Patent Application No. a201111426, dated Jun. 11, 2013, to the Office Action (Preliminary Conclusion on Non-patentability), 9 pages (with English Translation).
Response filed in U.S. Appl. No. 13/260,864, dated Aug. 1, 2017, including Request for Continued Examination, 51 pages.
Response filed in U.S. Appl. No. 13/260,864, dated Dec. 22, 2016, including Amendment, 22 pages.
Response filed in U.S. Appl. No. 13/260,864, dated Mar. 9, 2016 to the Final Office Action dated Nov. 20, 2015, including Amendment, 16 pages.
Response filed in U.S. Appl. No. 13/260,864, dated May 26, 2015, including Supplemental Amendment, Statement of Substance of Interview, and Applicant-Initiated Interview Summary dated Apr. 27, 2015, 17 pages.
Response filed in U.S. Appl. No. 13/260,864, dated Oct. 13, 2015, to the Non-Final Office Action dated Jul. 13, 2015, 17 pages.
Response filed in U.S. Appl. No. 13/260,864, including Amendment and Request for Continued Examination, dated Mar. 23, 2015, 23 pages.
Response filed in U.S. Appl. No. 13/260,864, including amendment, dated Sep. 9, 2014, 19 pages.
Response filed in U.S. Appl. No. 13/260,872, including amendments and two exhibits, dated Feb. 1, 2013, 167 pages.
Response filed in U.S. Appl. No. 14/061,426, dated Jul. 15, 2015, 4 pages.
Response filed in U.S. Appl. No. 14/061,426, dated Apr. 25, 2018, including Amendment and RCE, 32 pages.
Response filed in U.S. Appl. No. 14/061,426, dated Aug. 26, 2019 to the Final Office Action dated May 30, 2019, 7 pages.
Response filed in U.S. Appl. No. 14/061,426, dated Aug. 30, 2017 to the Office Action dated May 31, 2017, 48 pages.
Response filed in U.S. Appl. No. 14/061,426, dated Dec. 22. 2015, 125 pages.
Response filed in U.S. Appl. No. 14/061,426, dated Dec. 23, 2019 to the Final Office Action dated May 30, 2019, 50 pages.
Response filed in U.S. Appl. No. 14/061,426, dated Feb. 7, 2019, to the Office Action dated Nov. 19, 2018, 23 pages.
Response filed in U.S. Appl. No. 14/061,426, dated Mar. 17, 2020 to the Examiner's Answer dated Feb. 28, 2020, 3 pages.
Response filed in U.S. Appl. No. 14/061,426, dated Oct. 24, 2013, including Preliminary Amendment, 1 page.
Response filed in U.S. Appl. No. 14/061,426, dated Sep. 19, 2016, including RCE, ADS, and Amendment, 70 pages.
Response filed in U.S. Appl. No. 16/090,360, dated Jan. 10, 2020 to the Office Action, 9 pages.
Response filed in Vietnamese Patent Application No. 1-2011-02950, dated Dec. 13, 2013, 8 pages (with English Translation).
Response filed in Vietnamese Patent Application No. 1-2011-02950, dated May 30, 2016, 4 pages (with English Translation).
Response in Taiwanese Patent Application No. 099109838, dated Dec. 27, 2012 to the Office Action dated Jun. 22, 2012, 21 pages (with English Translation).
Restriction in U.S. Appl. No. 14/061,426, dated May 15, 2015, 7 pages.
Satsuka, "Recent evolution of liposome application," NTS, 2005, 16 pages (with English Translation).
Schöffski et al., "Activity of eribulin mesylate in patients with soft-tissue sarcoma: a phase 2 study in four independent histological subtypes," The Lancet Oncology, 2011, 12:1045-1052.
Sharpe et al., "The function of programmed cell death 1 and its ligands in regulating autoimmunity and infection," Nature Immunology, 2007, 8(3):239-245.
Shimauchi et al., "Augmented expression of programmed death-1 in both neoplastic and non-neoplastic $CD4^+$ T-cells in adult T-cell leukemia/lymphoma," Int. J. Cancer, 2007, 121:2585-2590.
Takahashi et al., "One-year follow-up results of eribulin for soft-tissue sarcoma including rare subtypes in a real-world observational study in Japan," Poster Display, Abstract No. 1683P displayed Sep. 28, 2019, European Society for Medical Oncology (ESMO) 2019 Congress, Barcelona, Spain, 1 page.

(56) References Cited

OTHER PUBLICATIONS

TheFreeDictionary.com [Online], "Residues," [Retrieved on Jul. 15, 2014], retrieved from: URL<http://medical-dictionary.thefreedictionary.com/p/Residues>, 2 pages.
Thompson et al., "PD-1 is expressed by tumor-infiltrating immune cells and is associated with poor outcome for patients with renal cell carcinoma," Clin. Cancer Res., 2007, 13(6):1757-1761.
Thompson et al., "Significance of B7-H1 Overexpression in Kidney Cancer," Clinical Genitourinary Cancer, 2006, 5(3):206-211.
Tolaney et al., "Phase 1b/2 study to evaluate eribulin mesylate in combination with pembrolizumab in patients with metastatic triple-negative breast cancer," [Abstract No. 177], Em. J. Cancer, 2017, 72:S16.
Twelves et al., "Efficacy of eribulin in women with metastatic breast cancer: a pooled analysis of two phase 3 studies," Breast Cancer Res. Treat., 2014, 148:553-561.
Voluntary Amendment filed in Cambodian Patent Application No. KH/P/10/00097, dated Jul. 7, 2016, 4 pages.
Wang et al. "Eribulin mesilate," Drugs of the Future, 2007, 32(8): 681-698.
Whatsthedose.com [online], "Normosol®-R pH 7.4—Packaging Insert," Hospira, Inc., revised Oct. 2006, [Retrieved on Jul. 20, 2012], retrieved from: URL<http://whatsthedose.com/spl/0409-7670.html>, 10 pages.
Written Opinion in International Patent Application No. PCT/JP2018/020456, dated Aug. 28, 2018, 15 pages (with English Translation).
Written Opinion in International Patent Application No. PCT/US2016/020734, dated Apr. 28, 2016, 8 pages.
Written Opinion in Singaporean Patent Application No. 11201706872S, dated Jun. 27, 2018, 7 pages.
Written Opinion in Singaporean Patent Application No. 11201706872S, dated Nov. 5, 2019, 10 pages.
Yamamoto et al., "Phase 1 study of liposomal formulation of eribulin (E7389-LF) in Patients with Advanced Solid Tumors: Primary Results of the Dose-Escalation Part," Poster Display, Abstract No. 348P, displayed Sep. 29, 2019, European Society for Medical Oncology (ESMO) 2019 Congress, Barcelona, Spain, 1 page.
Yang et al., "PD-L1 Interaction Contributes to the Functional Suppression of T-Cell Responses to Human Uveal Melanoma Cells In Vitro," Invest. Ophthalmol, Vis. Sci., 2008, 49(6):2518-2525.
Yi et al., "Biomarkers for predicting efficacy of PD-1/PD-L1 inhibitors," Molecular Cancer, 2018, 17:129.
Yin et al., "Enhanced Permeability and Retention (EPR) Effect Based Tumor Targeting: The Concept, Application and Prospect," JSM Clinical Oncology and Research, 2014, 2(1):1010.
Yu et.al., "Characterization of the pharmacokinetics of a liposomal formulation of eribulin mesylate (E7389) in mice," International Journal of Pharmaceutics, 2013, 443:9-16.
Zibelman et al., "Checkpoint Inhibitors and Urothelial Carcinoma: The Translational Paradigm," Oncology, 2016, 30(2):160-162.
Zucker et al., "Liposome drugs' loading efficiency: A working model based on loading conditions and drug's physicochemical properties," Journal of Controlled Release, 2009, 139(1):73-80.
Furnishing of Prescribed Information and Voluntary' Amendment and Payment of Fee for Grant in Singaporean Patent Application No. 201106388-0, dated Mar. 26. 2014, 17 pages.
Patent Certificate for Australian Patent No. 2014200717, granted on Jun. 9, 2016, 1 page.
Patent Certificate for Bruneian Patent No. RE-R-2017-0029, granted on Jul. 6, 2017, 1 page.
Patent Certificate for Canadian Patent No. 2,756,811, granted on Sep. 23, 2014, 2 pages.
Patent Certificate for Chilean Patent No. 56.288, granted on Jul. 3, 2018, 2 pages (with English Translation).
Patent Certificate for Chinese Patent No. ZL201080014698.2, granted on Oct. 29, 2,014, 3 pages (with English Translation).
Patent Certificate for Colombian Patent No. 4584, granted on Jan. 17, 2014, 2 pages (with English Translation).
Patent Certificate for European Patent No. 2415464, granted on May 10, 2017, 1 page.
Patent Certificate for European Patent No. 2415470, granted on Jul. 6, 2016, 1 page.
Patent Certificate for Hong Kong Patent No. HK 1165707, granted on Jul. 7, 2017, 2 pages.
Patent Certificate for Indian Patent No. 300213, dated Aug. 23, 2,018, 1 page.
Patent Certificate for Indonesian Patent No. IDP000045351. granted on Apr. 20, 2017, 66 pages (with English Translation).
Patent Certificate for Israeli Patent No. 215059, granted on Jul. 1, 2016, 4 pages.
Patent Certificate for Japanese Patent No. 5551683, granted on May 30, 2014, 4 pages (with English Translation).
Patent Certificate for Japanese Patent No. 5622719, granted on Oct. 3, 2014, 4 pages (with English Translation).
Patent Certificate for Japanese Patent No. 5770366, granted on Jul. 3, 2015, 4 pages (with English Translation).
Patent Certificate for Korean Patent No. 10-1495951, granted on Feb. 16, 2015, 4 pages (with English Translation).
Patent Certificate for Malaysian Patent No. MY-160203-A, granted on Febrary 28, 2017, 4 pages.
Patent Certificate for Mexican Patent No. 326330, granted on Dec. 15, 2014, 2 pages (with English Transla tion).
Patent Certificate for Moroccan Patent No. 33127, granted on Mar. 1, 2012, 3 pages (with English Translation).
Patent Certificate for New Zealand Patent No. 595212, granted on Jun. 4, 2014, 1 page.
Patent Certificate for Philippine Patent No. 1-2011-501838, granted on Nov. 25, 2015, 69 pages.
Patent Certificate for Russian Patent No. 2476216, granted on Feb. 27, 2013, 44 pages (with English Translation).
Patent Certificate for Singaporean Patent No. 174255, granted on Apr. 15, 2014, 2 pages.
Patent Certificate for South African Patent No. 2011-06535, granted on May 30, 2012, 3 pages.
Patent Certificate for Sri Lankan Patent No. 16427, granted on Aug. 6, 2014, 3 pages.
Patent Certificate for Taiwanese Patent No. 1392519, granted on Apr. 11, 2013, 3 pages (with English Translation).
Patent Certificate for Ukrainian Patent No. 103794, granted on Nov. 25. 2013, 32 pages (with English Translation).
Patent Certificate for U.S. Pat. No. 9,968,583, granted on May 15, 2018, 34 pages.
Patent Certificate for Vietnamese Patent No. 17167, granted on Jul. 4, 2017, 58 pages (with English Translation).
Request for Examination in Brazilian Patent Application No. PI10145273, dated Mar. 30, 2013, 6 pages (with English Translation).
Request for Examination in Chinese Patent Application No. 201080014698.2, dated Sep. 29, 2011, 5 pages (with English Translation).
Request for Examination in Chinese Patent Application No. 201880024121.6, dated Oct. 9, 2019, 2 pages (with English Translation).
Request for Examination in Colombian Patent Application No. 11-130828, dated Jul. 17, 2012, 2 pages (with English Translation).
Request for Examination in Egyptian Patent Application No. PCT1637-2011, dated Oct. 3, 2011, 1 page (with English Translation).
Request for Examination in Indian Patent Application No. 6850-DELNP-2011, dated Sep. 7, 2011, 6 pages.
Request for Examination in Indonesian Patent Application No. W-00201103470, dated Sep. 29, 2011, 2 pages (with English Translation).
Request for Examination in Japanese Patent Application No. 2011-507239, dated Jan. 10, 2013, 2 pages (with English Translation).
Request for Examination in Japanese Patent Application No. 2011-507240, dated Jan. 10, 2013, 2 pages (with English Translation).
Request for Examination in Japanese Patent Application No. 2014-92382, dated May 28, 2014, 2 pages (with English Translation).
Request for Examination in Japanese Patent Application No. 2018-514683, dated Apr. 17, 2020, 2 pages (with English Translation).

(56) References Cited

OTHER PUBLICATIONS

Request for Examination in Malaysian Patent Application No. PI2011004382, dated Sep. 15, 2011, 1 page.
Request for Examination in Russian Patent Application No. 2011139715, dated Sep. 29, 2011, 2 pages (with English Translation).
Request for Examination in Taiwanese Patent Application No. 147388, dated Mar. 30, 2013, 9 pages (with English Translation).
Request for Examination in Ukrainian Patent Application No. a201111426, dated Sep. 27. 2011, 2 pages (with English Translation).
Request for Examination in Vietnamese Patent Application No. 1-2011-02950, dated Oct. 31, 2011, 6 pages (with English Translation).
Response filed in Brazilian Patent Application No. PI10145273, dated Jul. 2, 2020, to the Office Action dated Mar. 30, 3030, 80 pages (with English Translation).
Communication pursuant to Article 94(3) EPC in European Patent Application No. 16710891.9, dated Nov. 16, 2020, 24 pages.
Letters Patent for the Brazilian Patent No. PI 1014527-3, granted on Nov. 24, 2020, 70 pages (with English Translation).
Notice of Allowance in U.S. Appl. No. 15/554,540, dated Nov. 4, 2020, 7 pages.
Notice of Intention to Refuse Patent Application in Singaporean Patent Application No. 11201706872S, dated Nov. 19, 2020, 11 pages.
Office Action in Mexican Patent Application No. MX/a/2017/011206, dated Nov. 24, 2020, 8 pages (with Partial Translation).
Office Action in U.S. Appl. No. 15/554,540, dated Aug. 11, 2020, 7 pages.
Response filed in U.S. Appl. No. 15/554,540, dated May 4, 2020, 23 pages.
Response filed in U.S. Appl. No. 15/554,540, dated Oct. 13, 2020, 7 pages.
Response filed in U.S. Appl. No. 15/554,540, dated Sep. 23, 2019, 38 pages.
Response filed in U.S. Appl. No. 16/835,719, dated Nov. 2, 2020, 7 pages.
Schmidt et al., "Assessment of Clinical Activity of PD-1 Checkpoint Inhibitor Combination Therapies Reported in Clinical Trials," JAMA Network Open, Feb. 2020, 3(2):e1920833.
ClinicalTrials.gov [online], "A Study of E7389 Liposomal Formulation (E7389-LF) Plus Nivolumab in Participants with Solid Tumor, History of Changes for Study: NCT04078295," Sep. 2019, retrieved from: URL<https://clinicaltrials.gov/ct2/history/NCT04078295?V_1=View#StudyPageTop, Sep. 2, 2019>, 4 pages.
Eisai Co., Ltd., News Release No. 20-54, "Eisai to present abstracts on oncology products and pipeline at ESMO Virtual Congress 2020," dated Sep. 11, 2020, 3 pages.
Eisai Co., Ltd., News Release No. 20-56, "Eisai presents latest data of phase I clinical trial on liposomal formulation of anti-cancer agent Halaven® (Eribulin) at ESMO Virtual Congress 2020," dated Sep. 18, 2020, 3 pages.
Iwasa et al., "Effect of infusion rate, premedication, and prophylactic peg-filgrastim treatment on the safety of the liposomal formulation of eribulin (E7389-LF): Results from the expansion part of a phase 1 study," Abstract 583P, Sep. 17, 2020, the European Society for Medical Oncology (ESMO) Virtual Congress, Sep. 19-21, 2020, Annals of Oncology (2020) 31 (suppl_4): S462-S504, 10.1016/annonc/annonc271, NPL277, 8 pages.
Iwasa et al., "Effect of infusion rate, premedication, and prophylactic peg-filgrastim treatment on the safety of the liposomal formulation of eribulin (E7389-LF): Results from the expansion part of a phase 1 study," E-poster for Abstract 583P, presented at the European Society for Medical Oncology (ESMO) Virtual Congress, Sep. 19-21, 2020, Annals of Oncology (2020) 31 (suppl_4):S462-S504, 10.1016/annonc/annonc271, 1 page.
Letters Patent for Patent No. 10271 in Algerian Patent Application No. 110640, dated Sep. 13, 2020, 4 pages (with English Translation).
Notice of Abandonment in U.S. Appl. No. 13/260,872, dated Dec. 3, 2013, 2 pages.
Notice of Allowance in Brazilian Patent Application No. PI10145273, dated Oct. 20, 2020, 2 pages (with English Translation).
Office Action in Brazilian Patent Application No. PI10145273, dated Jul. 14, 2020, 9 pages (with English Translation).
Office Action in Chinese Patent Application No. 201680025588.3, dated Jul. 7, 2020, 29 pages (with English Translation).
Office Action in Japanese Patent Application No. 2017-546075, dated Jul. 21, 2020, 6 page (with English Translation).
Office Action in U.S. Appl. No. 14/061,426, dated Sep. 1, 2020, 21 pages.
Patent Certificate for Bruneian Patent No. RE-R-2017-0029, granted on Jul. 4, 2017, 1 page.
Patent Certificate for Japanese Patent No. 5770336, granted on Jul. 3, 2015, 4 pages (with English Translation).
PCT International Search Report in International Patent Application No. PCT/JP2020/028663, dated Sep. 24, 2020, 20 pages (with English Translation).
Request for Examination in Brazilian Patent Application No. PI10145273, dated Dec. 27, 2011, 6 pages (with English Translation).
Request for Examination in Ukrainian Patent Application No. a201111426, dated Feb. 1, 2013, 2 pages (with English Translation).
Response filed in Brazilian Patent Application No. PI10145273, dated Jul. 2, 2020, to the Office Action dated Mar. 30, 2020, 80 pages (with English Translation).
Response filed in Brazilian Patent Application No. PI10145273, dated Oct. 6, 2020, to the Office Action dated Jul. 14, 2020, 20 pages (with English Translation).
Response filed in Peruvian Patent Application No. 001798-2015, dated Jul. 23, 2020, 15 pages (with English Translation).
Response filed in U.S. Appl. No. 16/835,719, dated Sep. 29, 2020, 10 pages.
Tamura et al., "Phase 1 study of the liposomal formulation of eribulin (E7389-LF): Results from the HER2-negative breast cancer expansion part," Eposter for Abstract 346P, presented at the European Society for Medical Oncology (ESMO) Virtual Congress, Sep. 19-21, 2020, Annals of Oncology (2020) 31(suppl_4):S348-S395, 10.1016/annonc/annonc268, 1 page.
Tamura et al., "Phase 1 study of the liposomal formulation of eribulin (E7389-LF): Results from the HER2-negative breast cancer expansion," Abstract 346P, dated Sep. 17, 2020, the European Society for Medical Oncology (ESMO) Virtual Congress, Sep. 19-21, 2020, Annals of Oncology (2020) 31(suppl_4):S348-S395, 10.1016/annonc/annonc268, 7 pages.
Tolaney et al., "Abstract PD6-13: Phase 1b/2 study to evaluate eribulin mesylate in combination with pembrolizumab in patients with metastatic triple-negative breast cancer," Cancer Research, Feb. 2018, vol. 78, 4 pages.
Office Action in U.S. Appl. No. 17/067,302, dated Dec. 30, 2020, 58 pages.
Official Decision in Egyptian Patent Application No. PCT1637/2011, dated Dec. 29, 2020, 10 pages (with English Translation).
Response filed in U.S. Appl. No. 14/061,426, dated Feb. 26, 2021, 27 pages.
Notice of Allowance in U.S. Appl. No. 17/067,302, dated Mar. 31, 2021, 8 pages.
Notice of Allowance in U.S. Appl. No. 16/835,719, dated Jan. 22, 2021, 10 pages.
Response filed in Egyptian Patent Application No. PCT1637/2011, dated Mar. 25, 2021, 17 pages (with English Translation).
Response filed in U.S. Appl. No. 17/067,302, dated Mar. 19, 2021, 15 pages.
Final Office Action in U.S. Appl. No. 14/061,426, dated Mar. 26, 2021, 19 pages.
Masuda et al., "Phase 1 Expansion Study of Liposomal Formulation of Eribulin (E7389-LF) for Solid Tumors: Focus on Breast Cancer," Abstract, The Japanese Society of Medical Oncology Annual Meeting, Feb. 10, 2021, p. 670.
Masuda et al., "Phase 1 Expansion Study of Liposomal Formulation of Eribulin (E7389-LF) for Solid Tumors: Focus on Breast Cancer,"

(56) References Cited

OTHER PUBLICATIONS

Presentation, The Japanese Society of Medical Oncology Annual Meeting, Feb. 21, 2021, 17 pages.
Notice of Allowance in Israeli Patent Application No. 254133, dated Jun. 3, 2021, 5 pages (with English Translation).
Notice of Allowance in U.S. Appl. No. 16/835,719, dated Jun. 14, 2021, 12 pages.
Notice of Allowance in U.S. Appl. No. 17/067,302, dated May 28, 2021, 11 pages.
Office Action in Australian Patent Application No. 2016226157, dated Jan. 29, 2021, 5 pages.
Office Action in Indian Patent Application No. 201747034283, dated Mar. 30, 2021, 3 pages (with English Translation).
Office Action in Israeli Patent Application No. 254133, dated Oct. 14, 2020, 7 pages (with partial translation).
Office Action in Japanese Patent Application No. 2017-546075, dated Mar. 23, 2021, 7 pages (with English Translation).
Office Action in Japanese Patent Application No. 2018-514683, dated Apr. 7, 2021, 9 pages (with English Translation).
Office Action in Mexican Patent Application No. MX/a/2017/011206, dated Mar. 12, 2021, 8 pages (with English Translation).
Office Action in Russian Patent Application No. 2019114459/04, dated Dec. 8, 2020, 12 pages (with English Translation).
Request for Continued Examination and Amendment in U.S. Appl. No. 14/061,426, dated Aug. 17, 2021, 21 pages.
Request for Continued Examination in U.S. Appl. No. 17/067,302, dated Apr. 12, 2021, 1 page.
Response filed in Egyptian Patent Application No. PCT1637/2011, dated Mar. 25, 2021, 26 pages (with English Translation).
Response filed in Japanese Patent Application No. 2018-514683, dated Aug. 5, 2021 to the Office Action dated Apr. 7, 2021, 10 pages (with English Translation).
Restriction Requirement in U.S. Appl. No. 16/341,579, dated Mar. 4, 2021, 10 pages.
Response filed in European Patent Application No. 17789632.1, dated Nov. 11, 2021, to the Communication pursuant to Article 94(3) EPC dated Sep. 20, 2021, 21 pages.
Official Decision in Egyptian Patent Application No. PCT1637/2011, dated Aug. 10, 2021, 8 pages (with English Translation).
Petition filed in Egyptian Patent Application No. PCT1637/2011, dated Sep. 28, 2021, 4 pages (with Partial English Translation).
[No Author], "PBA2021—31st International Symposium on Pharmaceutical and Biomedical Analysis—Aug. 29 (Sun)-Sep. 1 (Wed), Kyoto University at Katsura, Kyoto, Japan," available on or before Oct. 5, 2021, [Retrieved on Sep. 17, 2021], retrieved from: URL<http://soyaku.phar.kyushu-u.ac.jp/PBA2021/index.html#:~:text-The%20conference%20will%20be%20held,for%20Pharmaceutical%20and%20Biomedical%20Analysis.&text-We%20encourage%20also%20the%20young,meeting%20and%20present%20the%20results.>, 2 pages.
Communication pursuant to Article 94(3) EPC in European Patent Application No. 17789632.1, dated Sep. 20, 2021, 4 pages.
Eisai Co., Ltd., News Release No. 21-37, "Eisai To Present Data On Oncology Pipeline and Products At ASCO Annual Meeting," dated May 20, 2021, 5 pages.
Eisai Co., Ltd., News Release No. 21-73, "Eisai To Present Abstracts On Oncology Products and Pipeline At ESMO Virtual Congress 2021," dated Sep. 14, 2021, 3 pages.
Mano, "A separate determination of released and liposomal encapsulated eribulin in dog plasma by LC-MS/MS for its application to a pharmacokinetic study," Abstract, Global Drug Metabolism and Pharmacokinetics, Eisai Co., Ltd., Japan, 31st International Symposium on Pharmaceutical and Biomedical Analysis, Aug. 2021, 1 page.
Mano, "A separate determination of released and liposomal encapsulated eribulin in dog plasma by LC-MS/MS for its application to a pharmacokinetic study," Poster Display, Poster No. P-1, displayed Aug. 30, 2021, Global Drug Metabolism and Pharmacokinetics, Eisai Co., Ltd., Japan, 31st International Symposium on Pharmaceutical and Biomedical Analysis, 1 page.
Notice of Final Rejection in Japanese Patent Application No. 2018-514683, dated Sep. 15, 2021, 6 pages (with English Translation).
Yamaguchi et al., "Phase 1 study of the liposomal formulation of eribulin (E7389-LF): Results from the advanced gastric cancer expansion cohort," Abstract, 2021 ASCO Annual Meeting, Journal of Clinical Oncology, 2021, 39(Suppl. 15):4025.
Yamaguchi et al., "Phase 1 study of the liposomal formulation of eribulin (E7389-LF): Results from the advanced gastric cancer expansion cohort," Poster Display, Abstract No. 4025, displayed Jun. 4-8, 2021, 2021 ASCO Annual Meeting, Journal of Clinical Oncology, 2021, 1 page.
Yamamoto et al., "Phase 1b study of a liposomal formulation of eribulin (E7389-LF) + nivolumab (Nivo) in patients (pts) with advanced solid tumors," Abstract, ESMO Congress 2021, Annals of Oncology, 2021, 32(Suppl_5):S829-S866, 2 pages.
Yamamoto et al., "Phase 1b study of a liposomal formulation of eribulin (E7389-LF) + nivolumab (Nivo) in patients (pts) with advanced solid tumors," Poster Display, Poster No. 980P, displayed Sep. 16-21, 2021, ESMO Congress 2021, Annals of Oncology, 2021, 1 page.
Amendment filed in Japanese Patent Application No. 2018-514683, dated Dec. 7, 2021, 2 pages.
Decision to Grant in Thai Patent Application No. 1101002341, dated Nov. 15, 2021, 2 pages (with English Translation).
Request for Appeal in Japanese Patent Application No. 2018-514683, dated Dec. 7, 2021, 18 pages (with English Translation).
Administrative Appeal Against Rejection filed in Argentine Patent Application No. P100103420, dated Jan. 24, 2022, 19 pages (with English Translation).
Communication under Rule 71(3) in European Patent Application No. 17789632.1, dated Dec. 21, 2022, 33 pages.
Decision to Grant in Japanese Patent Application No. 2018-514683, dated Jan. 14, 2022, 4 pages (with English Translation).
Final Office Action in Argentine Patent Application No. P100103420, dated Oct. 7, 2020, 11 pages (with English Translation).
International Preliminary Report on Patentability in International Patent Application No. PCT/JP2020/028663, dated Feb. 10, 2022, 5 pages.
Letter of a Preliminary Acceptance in Jordanian Patent Application No. 0318/2020, dated May 30, 2018, 3 pages (with English Translation).
Letters Patent for Iranian Patent No. 83009, granted on Jun. 3, 2014, 2 pages (with English Translation).
Letters Patent for Iraqi Patent No. 3805, granted on Mar. 4, 2014, 2 pages (with English Translation).
Letters Patent for Jordanian Patent No. 3282, granted on Dec. 19, 2018, 2 pages (with English Translation).
Letters Patent for Lebanese Patent No. 9155, granted on Oct. 7, 2010, 2 pages (with English Translation).
Letters Patent for Thai Patent No. 85826, granted on Dec. 13, 2021, 2 pages (with English Translation).
Letters Patent for Yemeni Patent No. 196, granted on Nov. 25, 2017, 6 pages (with English Translation).
Mano, "A separate assay of released and liposomal encapsulated eribulin in dog plasma by liquid chromatography with tandem mass spectrometry for its application to a pharmacokinetic study," Journal of Separation Science, 2022, 10 pages.
Masuda et al., "Phase 1 study of the liposomal formulation of eribulin (E7389-LF): Results from the breast cancer expansion cohort," European Journal of Cancer, 2022, 168:108-118.
nih.gov [Online], "Nivolumab," Year introduced: 2019 (2010), [Retrieved on Jun. 4, 2022], retrieved from: URL<https://www.ncbi.nlm.nih.gov/mesh/?term=BMS-936558>, 2 pages.
Niwa et al., "Antitumor activity of liposomal formulation of eribulin combined with anti-PD-1," Poster Presentation No. 5584, Eisai Co., Ltd., Tsukuba, Japan, 1 page.
Notice of Allowance in South African Patent Application No. 2021/10686, dated Jul. 8, 2022, 2 pages.
Notice of Allowance in U.S. Appl. No. 14/061,426, dated Jan. 14, 2022, 21 pages.
Notice of Allowance in U.S. Appl. No. 14/061,426, dated Mar. 31, 2022, 11 pages.

(56) References Cited

OTHER PUBLICATIONS

Notice of Allowance in U.S. Appl. No. 14/061,426, dated Aug. 4, 2022, 11 pages.
Notice of Allowance in U.S. Appl. No. 14/061,426, dated Dec. 19, 2022, 12 pages.
Notice of Substantive Examination Fees in Gulf Cooperation Council Patent Application No. 2010/16760, dated Oct. 22, 2013, 2 pages (with English Translation).
Office Action in Argentine Patent Application No. P100103420, dated Jun. 9, 2021, 14 pages (with English Translation).
Office Action in European Patent Application No. 17789632.1, dated Jul. 12, 2022, 31 pages.
Office Action in Gulf Cooperation Council Patent Application No. 2010/16760, dated Sep. 16, 2014, 4 pages.
Office Action in Gulf Cooperation Council Patent Application No. 2010/16760, dated Jan. 26, 2014, 6 pages.
Office Action in Jordanian Patent Application No. 0381/2020, dated Apr. 23, 2018, 2 pages (with English Translation).
Office Action in Pakistani Patent Application No. 803/2010, dated Sep. 29, 2011, 2 pages.
Office Action in U.S. Appl. No. 17/563,162, dated Apr. 14, 2022, 5 pages.
Office Action in U.S. Appl. No. 17/563,162, dated Jun. 10, 2022, 113 pages.
Patent Certificate for Japanese Patent No. 7015237, granted on Jan. 25, 2022, 3 pages (with English Translation).
Patent Certificate for Peruvian Patent No. 10407, granted on Sep. 1, 2020, 2 pages (with English Translation).
Payment of Substantive Examination Fees in Gulf Cooperation Council Patent Application No. 2010/16760, dated Jan. 13, 2014, 2 pages (with English Translation).
Request for Continued Examination in U.S. Appl. No. 14/061,426, dated Feb. 10, 2022, 9 pages.
Request for Continued Examination in U.S. Appl. No. 14/061,426, dated Jun. 28, 2022, 3 pages.
Request for Continued Examination in U.S. Appl. No. 14/061,426, dated Oct. 7, 2022, 9 pages.
Response filed in Argentine Patent Application No. P100103420, dated Aug. 4, 2020, 53 pages (with English Translation).
Response filed in Argentine Patent Application No. P100103420, dated May 13, 2021, 23 pages (with English Translation).
Response filed in Egyptian Patent Application No. PCT 1637/2011, dated Jun. 27, 2022, 7 pages (with English Translation).
Response filed in European Patent Application No. 17789632.1, dated Nov. 9, 2022, 24 pages.
Response filed in Gulf Cooperation Council Patent Application No. 2010/16760, dated Aug. 24, 2014, 39 pages (with English Translation).
Response filed in Gulf Cooperation Council Patent Application No. 2010/16760, dated Jan. 21, 2015, 135 pages (with English Translation).
Response filed in Jordanian Patent Application No. 0318/2010, dated May 21, 2018, 15 pages (with English Translation).
Sato et al., "Phase 1 Dose Escalation Study of the Liposomal Formulation of Eribulin (E7389-LF) in Japanese Patients with Advanced Solid Tumors," Clinical Cancer Research, 2022, 30 pages.
Submission Document in European Patent Application No. 20847524.4, dated Jul. 25, 2022, 6 pages.
Submission Document in U.S. Appl. No. 17/563,162, dated May 31, 2022, 4 pages.
Substantive Examination in Argentine Patent Application No. P100103420, dated Nov. 6, 2019, 18 pages (with English Translation).
Topalian et al., "Safety, activity, and immune correlates of anti-PD-1 antibody in cancer," New England Journal of Medicine, 2012, 366(26):2443-2454.
Ahmed "Report from the 37th San Antonio Breast Cancer Symposium, Dec. 9-13, 2014, Texas, USA" Ecancermedicalscience, 4;9:508 (Feb. 2015).
Amendment filed in Australian Patent Application No. 2016226157, dated Aug. 11, 2020, 10 pages.
Amendment filed in Canadian Patent Application No. 2978311, dated Apr. 21, 2022, 2 pages.
Amendment filed in Canadian Patent Application No. 2978311, dated Mar. 2, 2021, 11 pages.
Amendment filed in European Patent Application No. 16710891.9, dated Aug. 10, 2020, 25 pages.
Amendment filed in European Patent Application No. 16710891.9, dated Feb. 18, 2020, 7 pages.
Amendment filed in European Patent Application No. 16710891.9, dated May 3, 2018, 11 pages.
Amendment filed in Japanese Patent Application No. 2017-546075, dated Mar. 4, 2019, 6 pages (with English translation).
Amendment filed in Korean Patent Application No. 10-2017-7027617, dated Feb. 23, 2021, 17 pages (with English translation).
Amendment filed in Korean Patent Application No. 10-2019-7013370, dated Aug. 3, 2020, 23 pages (with English translation).
Amendment filed in Singaporean Patent Application No. 11201706872S, dated Feb. 22, 2018, 12 pages.
Amendment filed in U.S. Appl. No. 15/554,540, dated Aug. 30, 2017, 9 pages.
Azvolinsky, "Immunotherapy Yields Response in Triple-Negative Breast Cancer," Cancer Network (Dec. 2014), 3 pages.
Azvolinsky, "Top 8 Highlights From SABCS 2014," Cancer Network (Dec. 2014), 2 pages.
Bai et al., "A guide to rational dosing of monoclonal antibodies," Clinical Pharmacokinetics, 51(2): 119-35 (Feb. 2012).
Bibliographic data of U.S. Appl. No. 62/128,373 (priority application) filed in opposition against EP3265122 dated Feb. 3, 2023.
Brewster et al. "Epidemiology, biology, and treatment of triple-negative breast cancer in women of African ancestry" The Lancet Oncology, 15(13): e625-e634 (2014).
Clinical Trial NCT01848834, History of Changes for Study: NCT01848834: Study of Pembrolizumab (MK-3475) in Participants with Advanced Solid Tumors (MK-3475-012/KEYNOTE-012) as published on Jan. 21, 2015, 10 pages.
Clinical trial NCT02513472: History of Changes for Study: NCT02513472: Study to Evaluation the Efficacy and Safety of Eribulin Mesylate in Combination with Pembrolizumab in Subjects with Metastatic Triple-Negative Breast Cancer (mTNBC) (study status: Nov. 12, 2015), 7 pages.
ClinicalTrials.gov, "History of Changes for Study: NCT02036502 Study of Pembrolizumab (MK-3475) in Combination With Lenalidomide and Dexamethasone in Participants With Multiple Myeloma (MK-3475-023/KEYNOTE023)," Jan. 2015, 5 pages.
ClinicalTrials.gov, "History of Changes for Study: NCT02039674: A study of pembrolizumab (MK-3475) in combination with chemotherapy or immunotherapy in participants with lung cancer (MK-3475-021/KEYNOTE-021)," (published on Feb. 25, 2015), 6 pages.
ClinicalTrials.gov, "History of Changes for Study: NCT02039674: A study of pembrolizumab (MK-3475) in combination with chemotherapy or immunotherapy in participants with non-small cell lung cancer (MK-3475-021/KEYNOTE-021)," Jan. 2015, 6 pages.
ClinicalTrials.gov, History of Changes for Study: NCT02142738 Study of Pembrolizumab (MK-3475) Compared to Platinum-Based Chemotherapies in Participants with Metastatic Non-Small Cell Lung Cancer (MK-3475-024/KEYNOTE-024), (published on Feb. 17, 2015, 19 pages.
ClinicalTrials.gov, "History of Changes for Study: NCT02305186: Safety and Immunological Effect of Pembrolizumab in Resectable or Borderline Resectable Pancreatic Cancer (UVA-PC-PD101)," (published on Nov. 27, 2014), 9 pages.
ClinicalTrials.gov, "History of Changes for Study: NCT02331368 Phase 2 Multi-center Study of Anti-PD-1 During Lymphopenic State After HDT/ASCT for Multiple Myeloma," Jan. 2015, 4 pages.
ClinicalTrials.gov, "History of Changes for Study: NCT02447003 Study of Pembrolizumab (MK-3475) Monotherapy for Metastatic Triple-Negative Breast Cancer (MK-3475-086/KEYNOTE-086)," (published on May 14, 2015), 10 pages.

(56) References Cited

OTHER PUBLICATIONS

Doherty et al., "Eribulin for the treatment of metastatic breast cancer: an update on its safety and efficacy" International Journal of Women's Health, 7, (Abstract) (Jan. 2015), 1 page.
Doherty et al., "Review: Eribulin for the treatment of metastatic breast cancer: an update on its safety and efficacy" International Journal of Women's Health, 7, 47-58 (Jan. 2015).
Dolan et al., "Review: PD-1 pathway inhibitors: changing the landscape of cancer immunotherapy," Cancer Control, 21(3), 231-237 (2014).
Dolgin, "Cancer's true breakthroughs" Nature Medicine, vol. 19(6): 660-663, Jun. 2013.
Eisai News Release: "U.S. FDA Approves Eisai's Halaventm (Eribulin Mesylate) Injection for Treatment of Metastatic Breast Cancer" Nov. 16, 2010, 2 pages.
Eisai Public Relations Department: "Eisai and Merck Enter Collaboration to Explore Novel Combination Regimens of Anti-PD-1 Therapy with Multi-targeting RTK Inhibitor and Microtubule Dynamics Inhibitor in Multiple Types of Cancer", Mar. 4, 2015, Tokyo, Japan and Kenilworth, NJ, USA, Retrieved from the Internet: URL: http://www.eisai.com/news/enews201518p, 8 pages.
Feature listings of claims 1, 6, 7, and 13 of the opposed patent, filed in opposition against EP3265122 dated Feb. 3, 2023, 2 pages.
Funahashi et al. "Eribulin mesylate reduces tumor microenvironment abnormality by vascular remodeling in preclinical human breast cancer models," Cancer Science, 105: 1334-1342 (2014).
Highlights of Prescribing Information of Halaven (eribulin mesylate), published Nov. 2010, 15 pages.
Highlights of Prescribing Information of Keytruda (pembrolizumab), published Sep. 2014, 16 pages.
Kalimutho, M. et al. "Review: Targeted therapies for triple-negative breast cancer: Combating a stubborn disease," Trends in Pharmacological Sciences, 36(12): 822-846 (Published online Nov. 1, 2015).
Kaufman et al, "Efficacy or eribulin in patients (ots) with metastatic breast cancer (MBC): A pooled analysis by HER2 and ER status," Journal of Clinical Oncology, 32 (26): 137-137 (2014).
Lehmann et al., "Identification and use of biomarkers in treatment strategies for triple-negative breast cancer subtypes," Journal of Pathology, 232: 142-150 (2014).
List of Citations filed in Israeli Patent Application No. 254133, dated Aug. 11, 2021, 11 pages.
List of Citations filed in Israeli Patent Application No. 254133, dated Aug. 18, 2021, 11 pages.
List of Citations filed in Israeli Patent Application No. 254133, dated Feb. 2, 2020, 9 pages.
List of Citations filed in Israeli Patent Application No. 254133, dated Nov. 17, 2019, 8 pages.
List of Citations filed in Israeli Patent Application No. 719562, dated Jul. 15, 2020, 3 pages.
Mancini et al., "Review: Standard of care and promising new agents for triple negative metastatic breast cancer," Cancers, 2014, 6(4):2187-2223.
Marm et al., "Targeted therapies in triple-negative breast cancer" Breast Care, 10(3): 159-166 (Jun. 2015).
McDermott et al. "Review: PD-1 as a potential target in cancer therapy" Cancer Medicine, 662-673 (2013).
Meeting Reporter at 37th Annual San Antonio Breast Cancer Symposium, Oncology Times, Feb. 10, 2015 issue, 3 pages.
Merck News Release: "Merck Receives Accelerated Approval of Keytruda ® (pembrolizumab), the first FDA-Approved Anti-PD-1 Therapy" Sep. 4, 2014, 3 pages.
Mittendorf et al., "PD-L1 Expression in Triple-Negative Breast Cancer," American Association for Cancer Research, 361-370, 2014.
Morikawa et al., "Review: Treating Triple-Negative Breast Cancer: Where Are We?" Journal of the National Comprehensive Cancer Network, 13(2), e8-e18 (Feb. 2015).
Mullard, "Learning from the 2012-2013 class of breakthrough therapies," Nature Reviews, 12: 891-893, Dec. 2013.
Muro et al. "Gastric cancer (GC) cohort of a phase 2 trial of E7389-LF (liposomal formulation of eribulin) in combination with nivolumab." American Society of Clinical Oncology—Gastrointestinal Cancers Symposium 2023, Abstract, Jan. 17, 2023, 1 page.
Muro et al. "Gastric cancer (GC) cohort of a phase 2 trial of E7389-LF (liposomal formulation of eribulin) in combination with nivolumab." American Society of Clinical Oncology—Gastrointestinal Cancers Symposium 2023, Poster, Jan. 17, 2023, 1 page.
Nanda et al., 2014 San Antonio Breast Cancer Symposium; S1-09; A phase 1b study of pembrolizumab (MK-3475) in patients with advanced triple-negative breast cancer (02 only abstract), 1508 pages.
Niwa et al. "Abstract 5584: Antitumor activity of liposomal formulation of eribulin combined with anti-PD-1," Cancer Res (2022), Jun. 15, 2022, 82(12_Supplement):5584, 4 pages.
Niwa et al. "Liposome-encapsulated eribulin shows enhanced antitumour activity over eribulin for combination therapy with anti-PD-1 antibody" Mol. Cancer Ther., https://doi.org/10.1158/1535-7163.MCT-22-0475, Jan. 24, 2023, 34 pages.
Notice of Abandonment in U.S. Appl. No. 16/341,579, dated Oct. 7, 2022, 2 pages.
Notice of Allowance in Australian Patent Application No. 2016226157, dated Jan. 18, 2022, 58 pages.
Notice of Allowance in Chinese Patent Application No. 201680025588.3, dated Dec. 31, 2020, 3 pages (with English translation).
Notice of Allowance in European Patent Application No. 16710891.9, dated Apr. 7, 2022, 3 pages.
Notice of Allowance in European Patent Application No. 16710891.9, dated Oct. 20, 2021, 149 pages.
Notice of Allowance in Israeli Patent Application No. 254133, dated Sep. 19, 2021, 2 pages (with English translation).
Notice of Allowance in Japanese Patent Application No. 2017-546075, dated Aug. 31, 2021, 6 pages (with English translation).
Notice of Allowance in Mexican Patent Application No. MX/a/2017/011206, dated Sep. 28, 2021, 2 pages (with English translation).
Notice of Allowance in U.S. Appl. No. 17/563,162, dated Jan. 20, 2023, 11 pages.
Notice of Allowance in U.S. Appl. No. 17/563,162, dated Oct. 26, 2022, 6 pages.
Notice of Allowance in U.S. Appl. No. 17/563,162, dated Sep. 15, 2022, 15 pages.
Office Action in Australian Patent Application No. 2016226157, dated Dec. 15, 2021, 2 pages.
Office Action in Australian Patent Application No. 2017342462, dated Jul. 20, 2021, 1 page.
Office Action in Australian Patent Application No. 2017342462, dated Oct. 1, 2021, 1 page.
Office Action in Brazilian Patent Application No. 112017018872-4, dated Sep. 21, 2021, 8 pages (with English translation).
Office Action in Canadian Patent Application No. 2978311, dated Jun. 3, 2022, 6 pages.
Office Action in Chinese Patent Application No. 2017800775257, dated Nov. 14, 2022, 2 pages.
Office Action in Chinese Patent Application No. 2017800775257, dated Nov. 21, 2022, 17 pages (with English translation).
Office Action in Chinese Patent Application No. 202080042486.9, dated Sep. 26, 2022, 13 pages (with English translation).
Office Action in European Patent Application No. 16710891.9, dated Feb. 17, 2023, 2 pages.
Office Action in European Patent Application No. 17800964.3, dated May 24, 2019, 3 pages.
Office Action in Indian Patent Application No. 201747034283, dated Apr. 27, 2021, 3 pages (with English translation).
Office Action in Israeli Patent Application No. 254133, dated Jan. 20, 2019, 4 pages (with English translation).
Office Action in Israeli Patent Application No. 719562, dated Mar. 15, 2020, 4 pages (with English translation).
Office Action in Israeli Patent Application No. 719562, dated Nov. 11, 2021, 6 pages (with English translation).

(56) References Cited

OTHER PUBLICATIONS

Office Action in Israeli Patent Application No. 719562, dated Oct. 26, 2022, 2 pages (with English translation).
Office Action in Israeli Patent Application No. 719562, dated Sep. 21, 2022, 2 pages (with English translation).
Office Action in Korean Patent Application No. 10-2017-7027617, dated Jan. 9, 2023, 11 pages (with English translation).
Office Action in Mexican Patent Application No. MX/a/2017/011206, dated Jul. 23, 2021, 4 pages (with English translation).
Office Action in Mexican Patent Application No. MX/a/2017/011206, dated Jul. 30, 2021, 4 pages (with English translation).
Office Action in Mexican Patent Application No. MX/a/2019/003994, dated Jul. 21, 2022, 12 pages (with English translation).
Office Action in Russian Patent Application No. 2017132877/04, dated Jan. 27, 2020, 8 pages (with English translation).
Office Action in Singaporean Patent Application No. 11201706872S, dated Jan. 21, 2021, 1 page.
Office Action in Singaporean Patent Application No. 11201706872S, dated Jul. 21, 2021, 1 page.
Office Action in Singaporean Patent Application No. 11201902974P, dated Apr. 29, 2021, 1 page.
Office Action in U.S. Appl. No. 15/554,540, dated Mar. 22, 2019, 12 pages.
Office Action in U.S. Appl. No. 16/341,579, dated Mar. 4, 2022, 9 pages.
Office Action in U.S. Appl. No. 17/563,162, dated Mar. 7, 2023, 2 pages.
Ooki et al. "The esophageal cancer cohort of a phase 2 trial of E7389-LF (liposomal formulation of eribulin) + nivolumab." American Society of Clinical Oncology—Gastrointestinal Cancers Symposium 2023, Abstract, Jan. 17, 2023, 1 page.
Ooki et al. "The esophageal cancer cohort of a phase 2 trial of E7389-LF (liposomal formulation of eribulin) + nivolumab." American Society of Clinical Oncology—Gastrointestinal Cancers Symposium 2023, Poster, Jan. 17, 2023, 1 page.
Opposition filed in European Patent Application No. 16710891.9, dated Feb. 8, 2023, 111 pages.
Opposition filed in European Patent Application No. 16710891.9, dated Feb. 9, 2023, 20 pages.
Opposition filed in European Patent Application No. 16710891.9, dated Jan. 23, 2023, 33 pages.
Opposition filed in European Patent Application No. 16710891.9, dated Jan. 27, 2023, 7 pages.
Park et al., "Clinical Benefits of and Recent Progress in Eribulin Mesylate Therapy for Breast Cancer Patients," Journal of Tumor, 2(4): 113-121 (Apr. 18, 2014).
Pembrolizumab Shows Potential in Breast Cancer, Cancer Discovery, 100-101 (Feb. 2015), 2 pages.
Poole, "Pembrolizumab: first global approval" Drugs, 74(16): 1973-1981 (2014).
Press release from Merck: dated May 30, 2014: "Merck Announces Generic Name for MK-3475, Merck's investigational anti-PD-1 Antibody: Pembrolizumab)," 2 pages.
Press Release Merck, Apr. 2013, "Merck announces breakthrough therapy designation for lambrolizumab an investigational antibody therapy for advanced melanoma," 6 pages.
Press Release Merck, Jul. 2013, "PD-1 inhibitor becomes 'Breakthrough Therapy'," Cancer Discovery 10, 4 pages.
Record of Assignments of U.S. Appl. No. 62/128,373 (priority application) filed in opposition against EP3265122, dated Feb. 3, 2023.
Request for Continued Examination in U.S. Appl. No. 17/563,162, dated Dec. 15, 2022, 6 pages.
Response filed in Australian Patent Application No. 2016226157, dated Jan. 5, 2022, 115 pages.
Response filed in Australian Patent Application No. 2016226157, dated Nov. 30, 2021, 15 pages.
Response filed in Brazilian Patent Application No. 112017018872-4, dated Dec. 16, 2021, 158 pages (with English translation).
Response filed in Chinese Patent Application No. 201680025588.3, dated Dec. 15, 2020, 8 pages (with English translation).
Response filed in Chinese Patent Application No. 201680025588.3, dated Sep. 22, 2020, 26 pages (with English translation).
Response filed in Chinese Patent Application No. 202080042486.9 dated Mar. 10, 2023, 47 pages (with English translation).
Response filed in European Patent Application No. 16710891.9, dated Dec. 23, 2019, 14 pages.
Response filed in European Patent Application No. 16710891.9, dated Jan. 26, 2021, 114 pages.
Response filed in Indian Patent Application No. 201747034283, dated Apr. 27, 2021, 1 page.
Response filed in Indian Patent Application No. 201747034283, dated Mar. 2, 2021, 2 pages.
Response filed in Indian Patent Application No. 201747034283, dated Nov. 24, 2020, 176 pages.
Response filed in Indian Patent Application No. 201747034283, dated Nov. 27, 2020, 71 pages.
Response filed in Israeli Patent Application No. 254133 dated Mar. 11, 2021, 81 pages (with English translation).
Response filed in Israeli Patent Application No. 254133, dated May 20, 2019, 12 pages (with English translation).
Response filed in Israeli Patent Application No. 289213, dated Oct. 13, 2022, 6 pages (with English translation).
Response filed in Israeli Patent Application No. 719562, dated Jul. 14, 2020, 10 pages (with English translation).
Response filed in Japanese Patent Application No. 2017-546075, dated Apr. 1, 2020, 29 pages (with English translation).
Response filed in Japanese Patent Application No. 2017-546075, dated May 21, 2021, 6 pages (with English translation).
Response filed in Japanese Patent Application No. 2017-546075, dated Oct. 15, 2020, 6 pages (with English translation).
Response filed in Japanese Patent Application No. 2019-518975, dated Sep. 28, 2020, 4 pages (with English translation).
Response filed in Mexican Patent Application No. MX/a/2017/011206, dated Jan. 22, 2021, 79 pages (with English translation).
Response filed in Mexican Patent Application No. MX/a/2017/011206, dated Jul. 15, 2021, 22 pages (with English translation).
Response filed in Mexican Patent Application No. MX/a/2017/011206, dated Jul. 27, 2021, 8 pages (with English translation).
Response filed in Mexican Patent Application No. MX/a/2017/011206, dated Sep. 28, 2021, 10 pages (with English translation).
Response filed in Russian Patent Application No. 2017132877/04, dated Jul. 27, 2020, 8 pages (with English translation).
Response filed in Russian Patent Application No. 2017132877/04, dated Nov. 28, 2019, 16 pages (with English translation).
Response filed in Singaporean Patent Application No. 11201706872S, dated Apr. 1, 2020, 18 pages.
Response filed in Singaporean Patent Application No. 11201706872S, dated Mar. 2, 2018, 19 pages.
Response filed in Singaporean Patent Application No. 11201706872S, dated Nov. 30, 2018, 17 pages.
Response filed in U.S. Appl. No. 15/554,540, dated Feb. 2, 2021.
Response filed in U.S. Appl. No. 15/554,540, dated Jan. 12, 2021, 3 pages.
Robert et al. "Drug of the year: programmed death-1 receptor/programmed death-1 ligand-1 receptor monoclonal antibodies," European Journal of Cancer, 49(14), 2968-2971 (2013).
Robert et al., "LBA-Pembrolizumab (pembro; MK-3475) for advanced melanoma: Randomized comparison of two dosing schedules" Annals of Oncology, Sep. 29, 2014, 25(5):1-41.
Shitara et al. "Phase I Study of the Liposomal Formulation of Eribulin (E7389-LF): Results from the Advanced Gastric Cancer Expansion Cohort" Clinical Cancer Research OF1-OF8. https://doi.org/10.1158/1078-0432.CCR-22-3027, Feb. 28, 2023, 8 pages.
Tanioka et al. "Anti-tumor activity of a liposomal formulation of Eribulin compared with the same dose of Eribulin in patient-derived breast cancer xenografts" San Antonio Breast Cancer Symposium—45th Annual Meeting, Abstract, Nov. 21, 2022, 1 page.
Tanioka et al. "Anti-tumor activity of a liposomal formulation of Eribulin compared with the same dose of Eribulin in patient-derived breast cancer xenografts" San Antonio Breast Cancer Symposium—45th Annual Meeting, Poster, Dec. 7, 2022, 2 pages.

(56) References Cited

OTHER PUBLICATIONS

Tolaney et al., "Abstract PD6-13: Phase 1b/2 study to evaluate eribulin mesylate in combination with pembrolizumab in patients with metastatic triple-negative breast cancer," Cancer Research, 78 (4 Suppl.), Abs. PD6-13 (2018).
Vahdat et al. "Eribulin mesylate + trastuzumab as first-line therapy for locally recurrent or metastatic HER2-positive breast cancer: results from a phase 2, multicenter, single-arm study," Cancer Research, 72 (24): Supp. 3. Abstract No. P5-20-04 (Dec. 15, 2012).
WHO Drug Information, vol. 27, No. 2, 2013 (excerpt on lambrolizumab (synonym for pembrolizumab), 115 pages.
Withdrawal issued in Japanese Patent Application No. 2019-518975, dated May 10, 2021, 2 pages (with English translation).
Corrected Notice of Allowability in U.S. Appl. No. 14/061,426, dated Apr. 27, 2023, 27 pages.
Niwa et al., "Session PO.IM01.15—Combination Immunotherapies 1-5075 / 9—Antitumor activity of liposomal formulation of eribulin combined with anti-human PD-1 antibody using hPBMC-humanized mouse models," Abstract, American Association for Cancer Research Annual, Mar. 31, 2023, 1 page.
Notice of Allowance in U.S. Appl. No. 14/061,426, dated Apr. 18, 2023, 29 pages.
Notice of Allowance in U.S. Appl. No. 17/563,162, dated Apr. 19, 2023, 7 pages.
Office Action in Chinese Patent Application No. 202080042486.9, dated Mar. 22, 2023, 11 pages (with English Translation).
Official Notification in U.S. Appl. No. 17/563,162, dated May 5, 2023, 2 pages.
Response filed in European Patent Application No. 17789632.1, dated Apr. 14, 2023, 3 pages.
Response filed in Pakistani Patent Application No. 803/2010, dated Nov. 22, 2022, 3 pages.
Response filed in U.S. Appl. No. 17/563,162, dated Apr. 25, 2023, 7 pages.
Notice of Allowance in U.S. Appl. No. 14/061,426, dated Jul. 28, 2023, 14 pages.
Amendment filed in Brazilian Patent Application No. 112021026170-2 dated Jun. 27, 2023, 21 pages.
Applicant-Initiated Interview Summary in U.S. Appl. No. 17/563,162, dated Aug. 16, 2022, 2 pages.
Azuma et al., "Phase 2 small cell lung cancer (SCLC) cohort of a phase 1b/2 trial of a liposomal formulation of eribulin in combination with nivolumab," Abstract No. 8593, Meeting Abstract I, 2023 ASCO Annual Meeting , published online May 31, 2023, 1 page.
Azuma et al., "The Small Cell Lung Cancer Cohort of a Phase 2 Trial of E7389-LF (Liposomal Formulation of Eribulin) + NivolumabE7389-Nivolumab", Poster Presentation at the American Society for Clinical Oncology Symposium; Jun. 2-6, 2023, Chicago, IL, USA, 1 page.
Extended European Search Report in European Patent Application No. 20847524.4, dated Jun. 19, 2023, 10 pages.
Office Action in U.S. Appl. No. 17/563,162, dated Jun. 13, 2023, 6 pages.
Patent Certificate for European Patent No. 3449921, granted on May 31, 2023, 2 pages.
Request for Continued Examination in U.S. Appl. No. 14/061,426, dated Jun. 15, 2023, 14 pages.
Response filed in Chinese Patent Application No. 202080042486.9, dated Jul. 4, 2023, 74 pages (with English Translation).
Response filed in U.S. Appl. No. 17/563,162, dated Aug. 26, 2022, 8 pages.
Response filed in U.S. Appl. No. 17/563,162, dated Jun. 29, 2023, 3 pages.
Response filed in U.S. Appl. No. 17/563,162, dated Sep. 28, 2022, 8 pages.
Response filed in U.S. Appl. No. 17/563,162, dated Sep. 29, 2022, 8 pages.
Response to Amendment under Rule 312 Communication and Examiner Interview Summary in U.S. Appl. No. 17/563,162, dated Oct. 7, 2022, 5 pages.
Terminal Disclaimer filed in U.S. Appl. No. 17/563,162, dated Jun. 27, 2023, 3 pages.
Office Action in Chinese Patent Application No. 202080042486.9, dated Aug. 22, 2023, 12 pages (with English Translation).
Office Action in U.S. Appl. No. 17/563,162, dated Aug. 24, 2023, 32 pages.
Olson et al., "Mouse Models for Cancer Immunotherapy Research," Cancer Discovery, Nov. 2018, 8(11):1358-1365.
Request for Reexamination in Chinese Patent Application No. 2020800424869, dated Dec. 5, 2023, 13 pages (with English Translation).
Response filed in European Patent Application No. 20847524.4, dated Dec. 6, 2023, 8 pages.
Response filed in Indonesian Patent Application No. P00202111802, dated Dec. 8, 2023 13 pages (with English Translation).
Kharkevich, "Pharmacology," Textbook for medical students, 10th edition corrected, revised, and supplemented, GEOTAR-Media, 2010, pp. 72-82 (with English Translation).
Office Action in Russian Patent Application No. 2021137703, dated Dec. 15, 2023, 25 pages (with English Translation).
Pokrovsky, "Small Medical Encyclopedia in 6 volumes," Medicine, 1996, vol. 4, pp. 81-83, vol. 5, pp. 90-96 with English Translation.
Office Action Vietnamese Patent Application No. 1-2021-08263, dated Feb. 29, 2024, 4 pages (with English Translation).
Kawakami et al., "Phase 2 small cell lung cancer cohort of liposomal eribulin given with nivolumab: Overall survival update, Abstract#: MO58-1," Japanese Society of Medical Oncology Annual Meeting (JSMO2024), Feb. 22-24, 2024, 11 pages.
Kawazoe et al., "Phase II Study of the Liposomal Formulation of Eribulin (E7389-LF) in Combination with Nivolumab: Results from the Gastric Cancer Cohort," Clinical Cancer Research, Apr. 1, 2024, 30(7):1264-1272.
Kawazoe et al., "Results of a phase 2 trial of E7389-LF + nivolumab in patients with gastric or esophageal cancers, Abstract#: MOS7-2," Japanese Society of Medical Oncology Annual Meeting (JSMO2024), Feb. 22-24, 2024, 13 pages.
Nishio et al., "Phase 2 Study of the Liposomal Formulation of Eribulin (E7389-LF) in Combination with Nivolumab: Results from the Small Cell Lung Cancer Cohort," Cancer Research Communications, 2024, 4(1):226-235.
Office Action in Taiwanese Patent Application No. 109125099, dated Mar. 25, 2024, 13 pages (with English Translation).
Tamura et al., "Combination activity of eribulin liposomal formulation and anti-PD-1 antibody after tumor regrowth during anti-PD-1 antibody treatment in mice, Poster#: 2955," American Association for Cancer Research (AACR) Annual Meeting 2024, Apr. 5-10, 2024, 1 page.
Yasojima et al., "E7389-LF as 1L chemotherapy for advanced/metastatic HER2-negative breast cancer (HER2-BC): Phase 1 dose-expansion study, Abstract #: MO9-3," Japanese Society of Medical Oncology Annual Meeting (JSMO2024), Feb. 22-24, 2024, 14 pages.
Yonemori et al., "E7389-LF as a First-line Chemotherapy for Patients With Metastatic/Advanced HER2-Negative Breast Cancer: Results From a Phase 1 Study Dose-Expansion Part, Poster #:405," European Society for Medical Oncology (ESMO) annual meeting, Oct. 20-24, 2024, 2023, 1 page.

* cited by examiner

METHOD FOR INHIBITING TUMOR GROWTH

TECHNICAL FIELD

The present invention relates to a method for inhibiting tumor growth by the administration of a liposome composition comprising eribulin or a pharmaceutically acceptable salt thereof.

BACKGROUND ART

Eribulin represented by formula (I) below is an inhibitor of microtubule dynamics that stops the cell cycle by inhibiting microtubule elongation. Eribulin is used as a drug in the treatment of breast cancer.

[Chemical Structure 1]

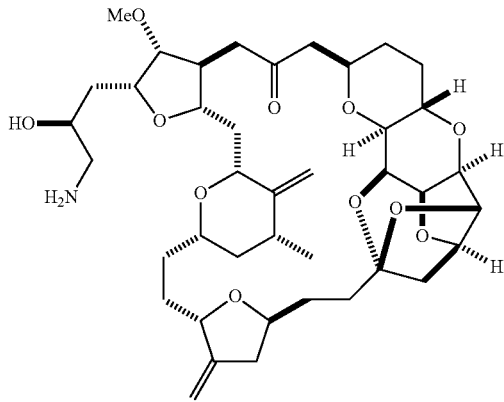

(I)

Patent Document 1 discloses eribulin or a pharmaceutically acceptable salt thereof and a method for producing the same.

Patent Document 2 and Patent Document 3 disclose methods for producing eribulin and eribulin mesylate which is mesylate (methanesulfonate) salt of eribulin.

Patent Document 4 discloses a method for inhibiting cancer growth in a patient by the administration to the patient of eribulin or a pharmaceutically acceptable salt thereof.

Patent Document 5 discloses a method for treating cancer in a patient by the administration to the patient of eribulin or a pharmaceutically acceptable salt thereof, in combination with a prescribed second anti-cancer agent.

Patent Document 6 discloses a method for treating cancer in a patient by the administration to the patient of eribulin or a pharmaceutically acceptable salt thereof, in combination with a second treatment means.

Patent Document 7 discloses a liposome composition comprising eribulin mesylate.

CITATION LIST

Patent Documents

Patent Document 1: WO 99/65894
Patent Document 2: WO 2005/118565
Patent Document 3: WO 2011/094339
Patent Document 4: U.S. Pat. No. 6,469,182
Patent Document 5: U.S. Patent Publication No. 2006/104984
Patent Document 6: U.S. Pat. No. 6,653,341
Patent Document 7: WO 2010/113984

SUMMARY

Technical Problem

The problem to be solved by the present invention is to provide a method for inhibiting the growth of certain tumors in patients.

Solution to Problem

As a result of intensive investigations, the present inventors discovered that the aforementioned problem can be solved by the administration to a patient of a liposome composition comprising eribulin or a pharmaceutically acceptable salt thereof. The present invention was achieved based on this discovery.

That is, the present invention is as follows.

[1]
A method of inhibiting growth of at least one tumor selected from the group consisting of uterine cancer (endometrial cancer, cervical cancer), esophageal cancer, pancreatic cancer, liver cancer (hepatocellular carcinoma, cholangiocarcinoma), biliary tract cancer, duodenal cancer, lung cancer (mesothelioma), kidney cancer (adrenal cortical carcinoma), sarcoma (liposarcoma, malignant fibrous histiocytoma, leiomyosarcoma, Ewing sarcoma), brain tumor (glioblastoma), urothelial cancer (bladder cancer), thyroid cancer, stomach cancer, and lymphoma in a patient, by administering to the patient a liposome composition comprising eribulin or a pharmaceutically acceptable salt thereof.

[2]
The method according to [1], wherein the eribulin or the pharmaceutically acceptable salt thereof is eribulin mesylate.

[3]
A pharmaceutical composition for inhibiting growth of at least one tumor selected from the group consisting of uterine cancer (endometrial cancer, cervical cancer), esophageal cancer, pancreatic cancer, liver cancer (hepatocellular carcinoma, cholangiocarcinoma), biliary tract cancer, duodenal cancer, lung cancer (mesothelioma), kidney cancer (adrenal cortical carcinoma), sarcoma (liposarcoma, malignant fibrous histiocytoma, leiomyosarcoma, Ewing sarcoma), brain tumor (glioblastoma), urothelial cancer (bladder cancer), thyroid cancer, stomach cancer, and lymphoma in a patient,
the pharmaceutical composition comprising a liposome composition comprising eribulin or a pharmaceutically acceptable salt thereof.

[4]
The pharmaceutical composition according to [3], wherein the eribulin or the pharmaceutically acceptable salt thereof is eribulin mesylate.

[5]
A therapeutic agent for at least one tumor selected from the group consisting of uterine cancer (endometrial cancer, cervical cancer), esophageal cancer, pancreatic cancer, liver cancer (hepatocellular carcinoma, cholangiocarcinoma), biliary tract cancer, duodenal cancer, lung cancer (mesothelioma), kidney cancer (adrenal cortical carcinoma), sarcoma (liposarcoma, malignant fibrous histiocytoma, leiomyosarcoma, Ewing sarcoma), brain tumor (glioblastoma), urothelial cancer (bladder cancer), thyroid cancer, stomach cancer, and lymphoma, the therapeutic agent comprising a liposome composition comprising eribulin or a pharmaceutically acceptable salt thereof.

[6]

The therapeutic agent according to [5], wherein the eribulin or the pharmaceutically acceptable salt thereof is eribulin mesylate.

Advantageous Effects of Invention

The present invention can provide a novel method of inhibiting the growth of certain tumors in patients by administering to the patient a liposome composition comprising eribulin or a pharmaceutically acceptable salt thereof.

DESCRIPTION OF EMBODIMENTS

Figure 1A:
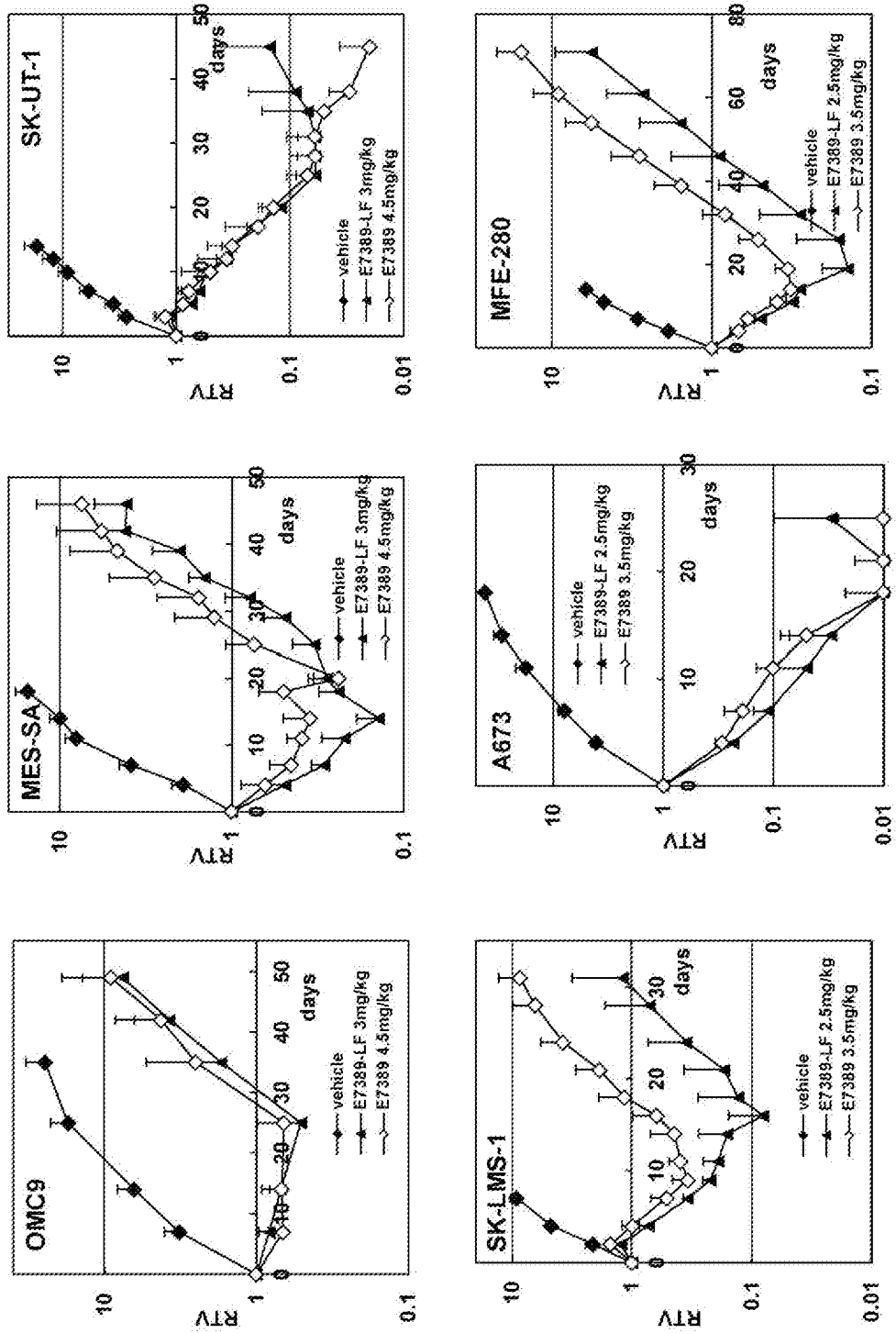
FIG. 1A shows the in vivo anti-tumor activity of a liposome composition comprising eribulin mesylate in nude mice with a different kind of tumor.

The present invention is more specifically described using embodiments of the invention. However, the present invention is not limited to the embodiments of the present invention described below and various modifications can be made.

The contents disclosed in the documents cited for the present invention are incorporated in the present invention by reference.

The liposome composition in the present invention comprises eribulin or a pharmaceutically acceptable salt thereof (hereinafter referred to as "eribulin, etc.").

In the present invention, the "pharmaceutically acceptable salt" may be an inorganic acid salt or an organic acid salt without particular limitation as long as a salt with eribulin is formed. Examples thereof include the chloride, sulfate, citrate, hydrobromide, hydroiodide, nitrate, bisulfate, phosphate, superphosphate, isonicotinate, acetate, lactate, salicylate, tartrate, pantothenate, ascorbate, succinate, maleate, fumarate, gluconate, saccharinate, formate, benzoate, glutamate, mesylate (methanesulfonate), ethanesulfonate, benzenesulfonate, p-toluenesulfonate, and pamoate, wherein the chloride, sulfate, acetate, phosphate, citrate, and mesylate are preferred and the mesylate is more preferred.

The pharmaceutically acceptable salt of eribulin may be a salt of eribulin with aluminum, calcium, lithium, magnesium, calcium, sodium, zinc, or diethanolamine.

Eribulin mesylate is preferred as the eribulin, etc. in the present invention.

Eribulin, etc. are the compound described in Patent Document 1 or U.S. Pat. No. 6,214,865 or salts thereof and have pharmacological activity, including anti-tumor activity and anti-mitotic activity. Patent Document 1 discloses that eribulin, etc. have, as anti-tumor agents, an anti-tumor activity for, e.g., melanoma, fibrosarcoma, monocytic leukemia, colon cancer, ovarian cancer, breast cancer, osteosarcoma, prostate cancer, lung cancer, and ras-transformed fibroblasts. Eribulin, etc. are obtained by the production methods described in Patent Documents 1 to 3.

In the present invention, "liposome" means a microscopic closed vesicle that has an internal phase enclosed by a lipid bilayer. Liposomes include, e.g., small unilamellar liposomes (SUV: small unilamellar vesicle), large unilamellar liposomes (LUV: large unilamellar vesicle), giant unilamellar liposomes (GUV: giant unilamellar vesicle), multilayer liposomes that have a plurality of concentric membranes (MLV: multilamellar vesicle), and liposomes that have a plurality of membranes that are not concentric but irregular (MVV: multivesicular vesicle).

In the present invention, "liposome internal phase" means an aqueous region enclosed by the lipid bilayer of the liposome and is used synonymously with "internal aqueous phase" and "liposome internal aqueous phase". "Liposome external phase" means a region not enclosed by the lipid bilayer of the liposome when the liposome is dispersed in a liquid (i.e., a region other than the internal phase and the lipid bilayer).

In the present invention, "liposome composition" means a composition comprising a liposome and further comprising eribulin, etc. in the liposome internal phase. In the present invention, the liposome composition includes a solid form composition and a liquid form composition.

In the present invention, "liposome dispersion" means a liposome-containing composition in which the eribulin, etc. is still not encapsulated into the liposome internal phase.

In the present invention, "liposome preparation solution" means a liposome-containing composition in which an adjustment of the liposome external phase in order to encapsulate the eribulin, etc. into the liposome internal phase is still not performed.

[Lipid]

In the present invention, the liposome preferably comprises, as a constituent component of the membrane, a phospholipid and/or a phospholipid derivative.

Examples of the phospholipid and phospholipid derivative include phosphatidylethanolamine, phosphatidylcholine, phosphatidylserine, phosphatidylinositol, phosphatidylglycerol, cardiolipin, sphingomyelin, ceramide phosphorylethanolamine, ceramide phosphorylglycerol, ceramide phosphorylglycerol phosphate, 1,2-dimyristoyl-1,2-deoxyphosphatidylcholine, plasmalogen, and phosphatidic acid.

The phospholipid and phospholipid derivative may be a single one of the preceding or may be a combination of two or more of the preceding.

The fatty acid residue in the phospholipid and phospholipid derivative is not particularly limited and examples thereof include the residues of saturated or unsaturated fatty acids having 12 to 20 carbons. Specific examples thereof include acyl groups derived from fatty acids such as lauric acid, myristic acid, palmitic acid, stearic acid, oleic acid, and linoleic acid. Also, phospholipids originating from natural substances, e.g., egg yolk lecithin and soy lecithin, and partially hydrogenated egg yolk lecithin, (completely) hydrogenated egg yolk lecithin, partially hydrogenated soy lecithin, and (completely) hydrogenated soy lecithin that are provided by partial or complete hydrogenation of unsaturated fatty acid residues, can be used as the phospholipid and phospholipid derivative.

The blending amount (mole fraction) of the phospholipid and/or phospholipid derivative used in liposome preparation is not particularly limited. However, it is preferably 10% to 80% and more preferably 30% to 60% based on the total components of the liposome membrane.

In the present invention, in addition to the phospholipid and/or phospholipid derivative, the liposome may also comprise, as a constituent component of the membrane, sterols such as cholesterol and cholestanol, fatty acids having a saturated or unsaturated acyl group having 8 to 22 carbons, and antioxidants such as α-tocopherol, as a membrane stabilizer.

The blending amount (mole fraction) of the sterol used in liposome preparation is not particularly limited. However, it is preferably 1% to 60%, more preferably 10% to 50%, and even more preferably 30% to 50% based on the total components of the liposome membrane.

The blending amount (mole fraction) of the fatty acid is not particularly limited. However, it is preferably 0% to 30%, more preferably 0% to 20%, and even more preferably 0% to 10% based on the total components of the liposome membrane.

The blending amount (mole fraction) of the antioxidant is not particularly limited as long as an amount to provide an antioxidant effect is added. However, it is preferably 0% to 15%, more preferably 0% to 10%, and even more preferably 0% to 5% based on the total components of the liposome membrane.

In the present invention, the liposome may comprise, as a constituent component of the membrane, a functional lipid or a modified lipid.

Examples of the functional lipid include long-circulating lipid derivatives, temperature-sensitive lipid derivatives, and pH-sensitive lipid derivatives.

Examples of the modified lipid include PEGylated lipids, glycolipids, antibody-modified lipids, and peptide-modified lipids.

Examples of the long-circulating lipid derivatives include polyethylene glycol derivatives (e.g., methoxypolyethylene glycol condensates) such as N-{carbony-lmethoxypolyethylene glycol-2000}-1,2-dipalmitoyl-sn-glycero-3-phosphoethanolamine, N-{carbonyl-methoxypolyethylene glycol-5000}-1,2-dipalmitoyl-sn-glycero-3-phosphoethanolamine, N-{carbonyl-methoxypolyethylene glycol-750}-1,2-distearoyl-sn-glycero-3-phosphoethanolamine, N-{carbonyl-methoxypolyethylene glycol-2000}-1,2-distearoyl-sn-glycero-3-phosphoethanolamine (MPEG2000-distearoylphosphatidylethanolamine), and N-{carbonyl-methoxypolyethylene glycol-5000}-1,2-distearoyl-sn-glycero-3-phosphoethanolamine, which are condensates of phosphoethanolamine and methoxypolyethylene glycol.

The blending amount (mole fraction) of the long-circulating lipid derivative used in liposome preparation is not particularly limited. However, it is preferably 0% to 50%, more preferably 0% to 30%, and even more preferably 0% to 20% based on the total components of the liposome membrane.

Examples of the temperature-sensitive lipid derivative include dipalmitoylphosphatidylcholine. The incorporation of a temperature-sensitive lipid derivative in the liposome makes it possible, for example, to disrupt the liposome at a prescribed temperature, to change the surface characteristics of the liposome at a prescribed temperature, and so forth. Moreover, by combining this with the application of heat at the target region, e.g., a tumor, the liposome can be disrupted at the target region and the active compound can be then released at the target region.

Examples of the pH-sensitive lipid derivative include dioleoylphosphatidylethanolamine. The incorporation of a pH-sensitive lipid derivative in the liposome makes it possible, for example, to promote membrane fusion between the liposome and endosome during intake of the liposome into a cell by endocytosis and thereby enhance delivery of the active compound to the cytoplasm.

Examples of the glycolipids, antibody-modified lipids, and peptide-modified lipids include lipids conjugated to sugars, antibodies or peptides which exhibit affinity for the target cell or target tissue. Use of the modified lipid enables active delivery of the liposome to the target cell or target tissue.

The composition of the constituent components of the membrane in order to provide a liposome having a practical level of membrane permeability can be determined as appropriate by the person having ordinary skill in the art according to, e.g., the active compound and the target tissue, with reference as necessary to the examples provided below (see, for example, Hiroshi Kikuchi, et al., "Liposome I—Preparative Methods and Test Methods—", Cell Technology, (1983) 2(9): pp. 1136-1149, and the references cited therein). In addition, the liposome composition can be used not only for the targeting to a target tissue such as a solid cancer, but also for the delivery of an active compound to, for example, a blood cancer.

The constituent components of the liposome membrane preferably comprise a phospholipid, cholesterol, and a methoxypolyethylene glycol condensate.

[Liposome Composition]

In the liposome composition of the present invention, eribulin, etc. is encapsulated in a liposome having a lipid membrane. The eribulin, etc. may be distributed into the lipid bilayer in the liposome composition.

The liposome composition of the present invention can be obtained by the methods described in Patent Document 7.

When the liposome composition is a solid form, the liquid liposome composition can be obtained by dissolution or suspension in a prescribed solvent as described below. In addition, when the liposome composition is a frozen solid, the liquid liposome composition can be obtained by, for example, leaving the solid at room temperature to melt.

The liposome composition of the present invention is not limited as long as it comprises (1) eribulin, etc. The liposome composition of the present invention may also comprise (2) at least one ammonium salt and (3) at least one acid, salt, base, and/or amino acid.

Examples of (2) the at least one ammonium salt include ammonium chloride, ammonium borate, ammonium sulfate, ammonium formate, ammonium acetate, ammonium citrate, ammonium tartrate, ammonium succinate, and ammonium phosphate, whereamong ammonium sulfate, ammonium citrate, and ammonium tartrate are preferred.

Examples of (3) the acid, salt, base, and/or amino acid include the following: as the acid, for example, ascorbic acid, benzoic acid, succinic acid, citric acid, glutamic acid, phosphoric acid, acetic acid, propionic acid, tartaric acid, carbonic acid, lactic acid, boric acid, maleic acid, fumaric acid, malic acid, adipic acid, hydrochloric acid, and sulfuric acid; as the salt, for example, sodium salts of the aforementioned acids, potassium salts of the aforementioned acids, and ammonium salts of the aforementioned acids; as the base, for example, trishydroxymethylaminomethane, ammonia, sodium hydroxide, and potassium hydroxide; and as the amino acid, for example, arginine, histidine, and glycine.

(3) The acid, salt, base, and/or amino acid in the liposome internal phase is preferably hydrochloric acid, acetic acid, lactic acid, tartaric acid, succinic acid, citric acid, and phosphoric acid, sodium salts of the above acids, and sodium hydroxide and ammonia, and more preferably acetic acid, lactic acid, tartaric acid, citric acid, and phosphoric acid and sodium salts of the above acids and sodium hydroxide and ammonia.

Table 1 gives an example of the individual components in the liposome composition. In another specific example, 96 mg/mL sucrose can be used in place of the 9 mg/mL sodium chloride as an osmotic agent (liposome external phase).

TABLE 1

| Component | Concentration | Purpose of blend |
| --- | --- | --- |
| eribulin mesylate | 0.2 mg/mL | drug |
| HSPC[1] | 7.1 mg/mL | lipid membrane component |
| cholesterol | 2.3 mg/mL | lipid membrane component |
| MPEG2000-DSPE[2] | 2.7 mg/mL | lipid membrane component |
| ammonium sulfate | 100 mM | liposome internal phase component |
| citric acid monohydrate | 30 mM | liposome internal phase component |
| sodium chloride | 9 mg/mL | liposome external phase component |
| L-histidine | 1.6 mg/mL | liposome external phase component |
| sodium hydroxide/ hydrochloric acid | suitable amount | pH modifier |

[1]hydrogenated soy phosphatidylcholine [2]N-{carbonylmethoxypolyethylene glycol-2000}-1,2-distearoyl-sn-glycero-3-phosphoethanolamine (MPEG2000-distearoylphosphatidylethanolamine)

[Pharmaceutical Composition]

The liposome composition of the present invention can be used as an anti-tumor agent pharmaceutical composition.

When the liposome composition of the present invention is used as a pharmaceutical composition, the liposome composition may be administered by injection (intravenous, intra-arterial, or topical injection), or oral, nasal, or transdermal administration, or by inhalation or as eye drops. In particular, injections, e.g., intravenous injection, subcutaneous injection, intradermal injection, and intra-arterial injection as well as topical injection to targeted cells or an organ are preferred. Examples of the dosage form of the liposome composition to be orally administered include tablet, powder, granulate, syrup, capsule, and internal liquid agent. Examples of the dosage form of the liposome composition to be parenterally administered include injectable agents, drip infusion agents, eye drops, ointments, suppositories, suspensions, cataplasms, lotions, aerosols, and plasters. Among them, injectable agents and drip infusion agents are preferred.

When the liposome composition is a liquid, it may be used as it is. When the liposome composition is to be used as a drug, preparation at the time of use can be carried out, for example, by having the physician or patient inject a solvent into a vial loaded with the solid formulation. In the case of a solid formulation provided by freezing the liquid liposome composition, storage may be carried out in the frozen state and the liquid agent can be then provided for use by returning to the liquid state at the time of use by leaving it at room temperature to melt or by heating it to rapidly melt.

The dose of the pharmaceutical composition varies substantially depending, inter alia, on the target disease, the age, sex, and weight of the patient, and the severity of the symptoms. The dose of the eribulin, etc. is not particularly limited. However, the dose of eribulin mesylate, which is a suitable salt, is generally 0.1 to 10 mg/m$^2$ (body surface area) per day for adults. Eribulin mesylate is preferably administered at a dose of 0.5 to 3 mg/m$^2$ (body surface area) once every 1 week, 2 weeks, or 3 weeks. Eribulin mesylate is more preferably administered at a dose of 0.5 to 2 mg/m$^2$ (body surface area) once every 1 week, 2 weeks, or 3 weeks.

In another embodiment, eribulin mesylate is preferably administered at a dose of approximately 1.5 mg/m$^2$ (body surface area) once every 1 week, 2 weeks, or 3 weeks.

More specifically, the dose of eribulin mesylate in the liposome composition is 0.5 to 1.4 mg/m$^2$ on day 1 of a 21 day cycle by intravenous administration or 0.5 to 1.5 mg/m$^2$ on day 1 and day 15 of a 28 day cycle by intravenous administration.

The eribulin, etc. in the liposome composition may be administered once per day or the daily dose may be administered over several administrations.

For example, a liposome composition comprising 0.01 to 300 mg/mL of eribulin, etc. in the liposome internal phase can be administered as the pharmaceutical composition of the present invention.

In a specific example of an injectable pharmaceutical composition of the present invention, it is formulated as an injectable agent comprising 0.20 mg/mL eribulin mesylate (0.18 mg/mL eribulin) encapsulated in a liposome having a lipid membrane comprising HSPC, cholesterol, and MPEG2000-DSPE. This pharmaceutical composition also comprises sucrose or sodium chloride as a tonicity agent, ammonium sulfate, citric acid, and L-histidine and sodium hydroxide and hydrochloric acid for pH adjustment. This pharmaceutical composition may be directly administered to a patient or may be diluted, prior to administration to a patient, with physiological saline into the concentration range from 0.0035 mg/mL to less than 0.2 mg/mL.

[Tumor Types]

The type of tumors that may be targeted by the method of the present invention for inhibiting tumor growth is at least one tumor selected from the group consisting of uterine cancer (endometrial cancer, cervical cancer), esophageal cancer, pancreatic cancer, liver cancer (hepatocellular carcinoma, cholangiocarcinoma), biliary tract cancer, duodenal cancer, lung cancer (mesothelioma), kidney cancer (adrenal cortical carcinoma), sarcoma (liposarcoma, malignant fibrous histiocytoma, leiomyosarcoma, Ewing sarcoma), brain tumor (glioblastoma), urothelial cancer (bladder cancer), thyroid cancer, stomach cancer, and lymphoma.

Preferred tumor types are uterine cancer (endometrial cancer, cervical cancer), pancreatic cancer, liver cancer (hepatocellular carcinoma, cholangiocarcinoma), biliary tract cancer, sarcoma (liposarcoma, leiomyosarcoma, Ewing sarcoma), brain tumor (glioblastoma), urothelial cancer (bladder cancer), thyroid cancer, and stomach cancer.

More preferred tumor types are uterine cancer (endometrial cancer, cervical cancer), pancreatic cancer, hepatocellular carcinoma, leiomyosarcoma, Ewing sarcoma, glioblastoma, urothelial cancer (bladder cancer), thyroid cancer, and stomach cancer.

Even more preferred tumor types are uterine cancer (endometrial cancer, cervical cancer), pancreatic cancer, leiomyosarcoma, urothelial cancer (bladder cancer), and stomach cancer.

EXAMPLES

The present invention is specifically described using examples and comparative examples, but the present invention is not limited to the examples provided below.

Example 1

An eribulin mesylate-containing liposome composition (hereinafter also referred to as "E7389-LF") was produced using the following procedure and the components described in Table 1. The obtained E7389-LF was evaluated for its anti-tumor activity.

<Preparation of Aqueous Solution for Liposome Internal Phase>

Ammonium sulfate and citric acid monohydrate were dissolved in pure water and were diluted to produce a 200 mM ammonium sulfate/60 mM citric acid aqueous solution. The pH of the 200 mM ammonium sulfate/60 mM citric acid aqueous solution was adjusted to pH 5.5 using aqueous ammonia, followed by dilution using pure water to yield a 100 mM ammonium sulfate/30 mM citric acid aqueous solution.

<Preparation of the Liposome Preparation Solution>

Hydrogenated soy phosphatidylcholine, cholesterol, and MPEG2000-distearoylphosphatidylethanolamine were each weighed out according to the weight ratio 71:23:27. Each was dissolved in chloroform and these solutions were mixed, followed by distillative removal of the chloroform under reduced pressure using a rotary evaporator to produce a lipid film. The prepared aqueous solution for the liposome internal phase was heated to approximately 80° C. and added to the obtained lipid film and a liposome preparation solution was prepared by stirring. Sizing was performed using an extruder (Lipex Biomembranes Inc.) heated to approximately 80° C. to obtain a sized liposome preparation solution.

<Preparation of Liposome Dispersion>

Using a Sephadex G-50 column, the obtained liposome preparation solution was eluted with a 0.9% sodium chloride/10 mM histidine aqueous solution (pH=7.6) to replace the liposome external phase with the 0.9% sodium chloride/10 mM histidine aqueous solution. After the replacement of the liposome external phase, centrifugation was carried out for 30 minutes at 400,000×g. Centrifugation was followed by redispersion and adjustment of the volume of the liquid using the 0.9% sodium chloride/10 mM histidine aqueous solution to obtain the liposome dispersion.

<Preparation of Eribulin Mesylate Solution>

An eribulin mesylate solution was obtained by dissolving eribulin mesylate in a 0.9% sodium chloride/10 mM histidine aqueous solution.

<Preparation of Liposome Composition>

The liposome dispersion and the eribulin mesylate solution were mixed in a glass vessel and incubation was carried out for 3 minutes in a 60° C. water bath to obtain a liposome composition in which eribulin mesylate was introduced into the liposome internal phase. A 0.9% sodium chloride/10 mM histidine aqueous solution was added to the liposome composition and filtration sterilization was carried out using a 0.22 μm polyvinylidene fluoride (PVDF) filter to obtain liposome compositions at the eribulin mesylate target concentrations of from 0.1 mg/mL to 0.5 mg/mL (for example, 0.24 mg/mL, 0.3 mg/mL, 0.5 mg/mL).

<Preparation of Eribulin Mesylate Aqueous Solution>

Eribulin mesylate was dissolved in a 0.9% sodium chloride/10 mM histidine aqueous solution to obtain 5 mg/mL and 3.5 mg/mL eribulin mesylate aqueous solutions (hereinafter also referred to as "E7389").

<Measurement of Anti-Tumor Activity>

Cancer cell lines were purchased from the Riken Bioresource Center (RBC, Japan (Ibaraki)), American Type Culture Collection (ATCC, USA (Manassas, Va.)), Deutsche Sammlung von Mikroorganismen and Zellkulturen GmbH (German Collection of Microorganisms and Cell Cultures GmbH: DSMZ, Germany (Braunschweig)), Health Science Research Resource Bank (HSRRB, Japan (Osaka)), and the DS Pharma Biomedical Co., Ltd. (DS-Pharma, Japan (Osaka)), and were kindly donated by the Kyushu Cancer Center, Kagoshima University, and the Cell Resource Center for Biomedical Research of the Institute of Development, Aging, and Cancer of Tohoku University.

The culture conditions and transplant conditions for the individual cancer cell lines are given in Tables 2 and 3. In the tables, the cancer cell lines to which "*" is added in the "acclimation" column were obtained from grown tumors which were formed by subcutaneously inoculating each cancer cell line to a mouse in advance.

The KB cells indicated as a cancer cell line in Table 2 were originally thought to be derived from an epithelial cancer. In recent years, however, they were proved to be a contamination of HeLa cells (cervical cancer) (http://wvvw.atcc.org/products/all/CCL-17.aspx#characteristics). In addition, ITS-G supplement (Wako Pure Chemical Industries, Ltd., #090-06741) was used as the ITS.

TABLE 2

| cancer cell line | origin | source | acclimation |
|---|---|---|---|
| CMC9 | sarcoma (leiomyosarcoma) | RBC | |
| MES-SA | sarcoma (leiomyosarcoma) | ATCC | |
| SK-UT-1 | sarcoma (leiomyosarcoma) | ATCC | + |
| SK-LMS-1 | sarcoma (leiomyosarcoma) | ATCC | + |
| A673 | sarcoma (Ewing sarcoma) | ATCC | |
| MFE-280 | uterine cancer (endometrial cancer) | DSMZ | |
| MFE-296 | uterine cancer (endometrial cancer) | DSMZ | |
| HEC-151 | uterine cancer (endometrial cancer) | HSRRB | |
| ECC-1 | uterine cancer (endometrial cancer) | ATCC | |
| KB(HeLa) | uterine cancer (cervical cancer) | Kagoshima University, Aklyama | |
| AsPC-1 | pancreatic cancer | ATCC | |
| BXPC-3 | pancreatic cancer | ATCC | |
| KP-1 | pancreatic cancer | Kyushu Cancer Center, Funakoshi | |
| K1 | thyroid cancer | DS-Pharma | |
| U251MG | brain tumor (glioblastoma) | RBC | + |
| PLC/PRF/5 | liver cancer (hepatocellular carcinoma) | Cell Resource Center for Biomedical Research, Institute of Development, Aging, and Cancer, Tohoku University | |
| Hs746T | stomach cancer | ATCC | |
| UM-UC-3 | urothelial cancer (bladder cancer) | DS-Pharma | |

TABLE 2-continued

| cancer cell line | culture medium | no. of transplanted cells × 10⁸ cells/spot | use of GelTrex during cell transplantation | tumor volume at start of treatment (mm³) |
|---|---|---|---|---|
| CMC9 | HamF 12/10% FBS | 8.7 | + | 150 |
| MES-SA | McCoy5A/10% FBS | 6.3 | + | 190 |
| SK-UT-1 | EMEM/10% FBS, pyruvate, NEAA | 10 | − | 260 |
| SK-LMS-1 | EMEM/10% FBS, pyruvate, NEAA | 4.5 | − | 290 |
| A673 | DMEM(high glucose)/10% FBS, pyruvate | 10 | − | 220 |
| MFE-280 | RPMI1640:EMEM = 1:1/20% FBS, ITS | 10 | + | 200 |
| MFE-296 | RPMI1640:EMEM = 1:1/20% FBS, ITS | 5 | + | 200 |
| HEC-151 | EMEM/15% FBS | 5 | + | 220 |
| ECC-1 | EMEM/15% FBS | 10 | + | 160 |
| KB(HeLa) | RPMI1640/10% FBS | 5 | − | 150 |
| AsPC-1 | RPMI1640/10% FBS | 10 | − | 380 |
| BXPC-3 | DMEM (high glucose)/10% FBS, pyruvate | 10 | − | 120 |
| KP-1 | RPMI1640/10% FBS | 9 | + | 200 |
| K1 | DMEM:F12 = 1:1/10% FBS | 5 | + | 390 |
| U251MG | RPMI1640/10% FBS | 11 | + | 150 |
| PLC/PRF/5 | DMEM(high glucose)/10% FBS, pyruvate | 10 | + | 180 |
| Hs746T | DMEM(high glucose)/10% FBS, pyruvate | 10 | + | 180 |
| UM-UC-3 | EMEM/10% FBS pyruvate, NEAA | 10 | + | 230 |

TABLE 3

| cancer cell line | origin | source | acclimation | culture medium | no. of transplanted cells × 10⁸ cells/spot | use of GelTrex during cell transplantation | tumor volume at start of treatment (mm³) |
|---|---|---|---|---|---|---|---|
| MES-SA | sarcoma (leiomyosarcoma) | ATCC | | McCoy5A/10% FBS | 10 | + | 420 |
| SK-UT-1 | sarcoma (leiomyosarcoma) | ATCC | + | EMEM/10% FBS, pyruvate, NEAA | 10 | − | 290 |
| UM-UC-3 | urothelial cancer (bladder cancer) | DS-Pharma | | EMEM/10% FBS, pyruvate, NEAA | 5 | + | 190 |

On the initial day of inoculation, the cancer cells were harvested by trypsinization and were washed and suspended using the particular medium. Some of the harvested cancer cells were then mixed with GelTrex (Gibco, #12760-021 or A14132-02) at 1:1. Using a 26-gauge syringe needle, these cells were inoculated at a volume of 0.1 mL into the vicinity of the right axillary region of mice (BALB/c nu/nu).

After the tumor volume had reached from 120 mm³ to 420 mm³, the mice were divided into groups (day 0) such that the tumor volume and mouse body weight were substantially equal among the test groups (5 to 9 mice per test group). The initial average tumor volume (TV at day 0) for each model is given in Table 2 and Table 3 as the tumor volume (mm³) at the start of treatment.

Immediately before administration after the division into groups, the E7389-LF or E7389 was diluted with physiological saline to prepare the administration sample. The administration sample was administered intravenously, at an administration volume of 0.1 mL per 10 g body weight, after the division into groups (day 0) and 7 days after the division into groups.

The tumor size was measured over time with a caliper, and the tumor volume was determined based on the following calculation formula.

$$\text{tumor volume (mm}^3\text{)} = \text{length (mm)} \times \text{square of width (mm}^2\text{)} \times \tfrac{1}{2}$$

length: longest diameter of tumor
width: diameter perpendicular to length relative tumor volume (RTV)=tumor volume (day X)/tumor volume (day 0)

The average±SD of the tumor volume was calculated for each test group.

Figure 1B:
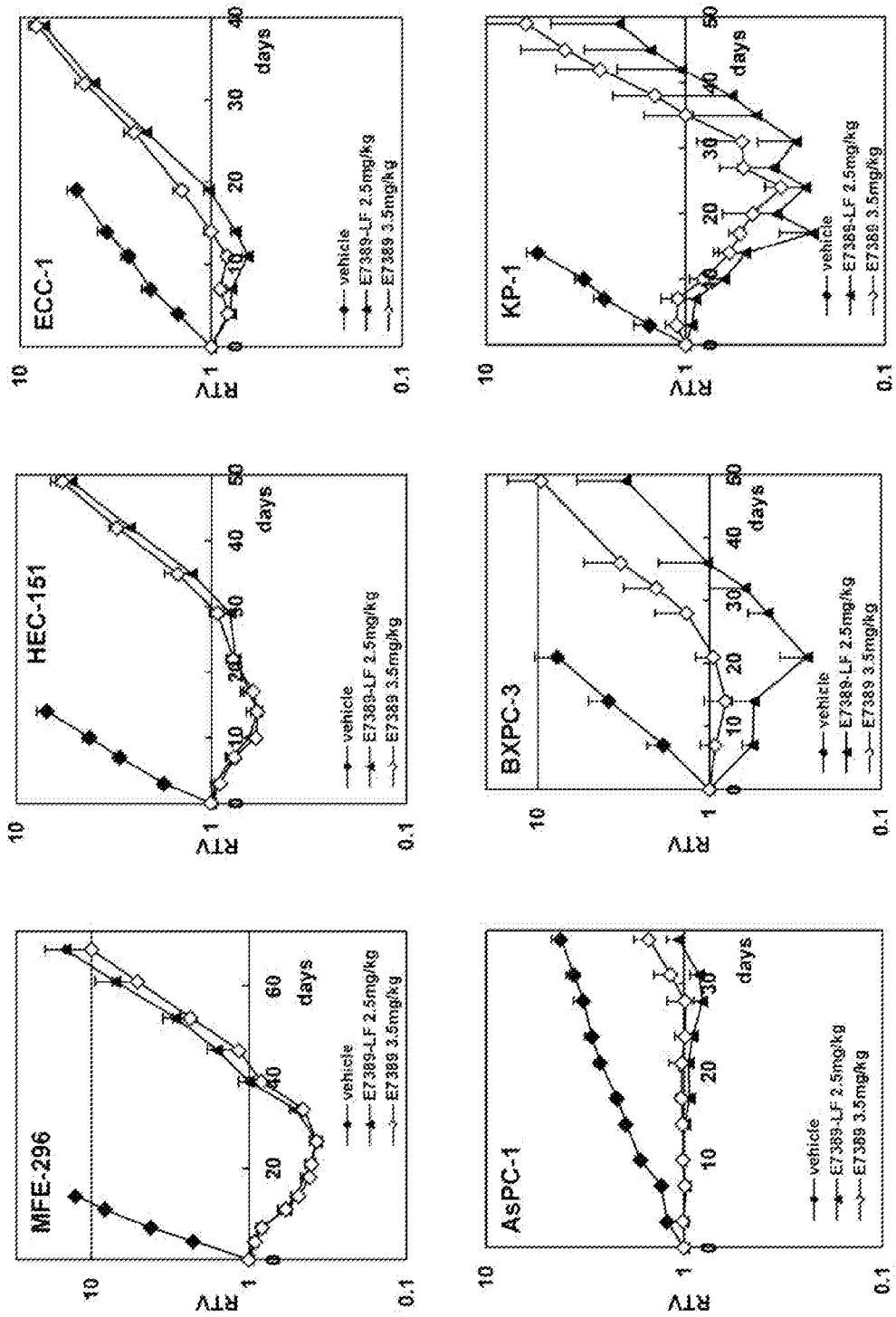
FIG. 1B shows the in vivo anti-tumor activity of a liposome composition comprising eribulin mesylate in nude mice with a different kind of tumor.
Figure 1C:
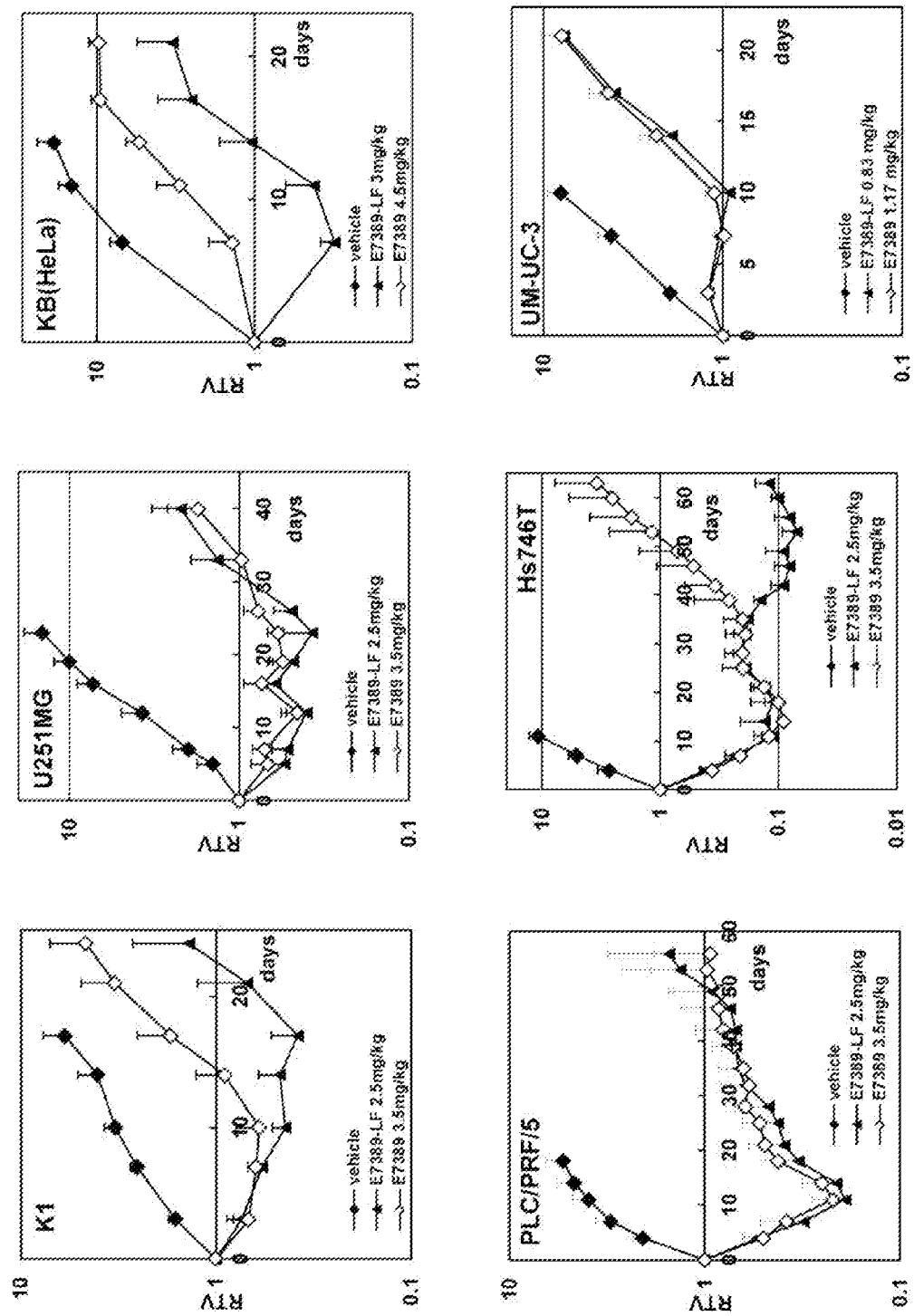
FIG. 1C shows the in vivo anti-tumor activity of a liposome composition comprising eribulin mesylate in nude mice with a different kind of tumor.
Figure 1D:
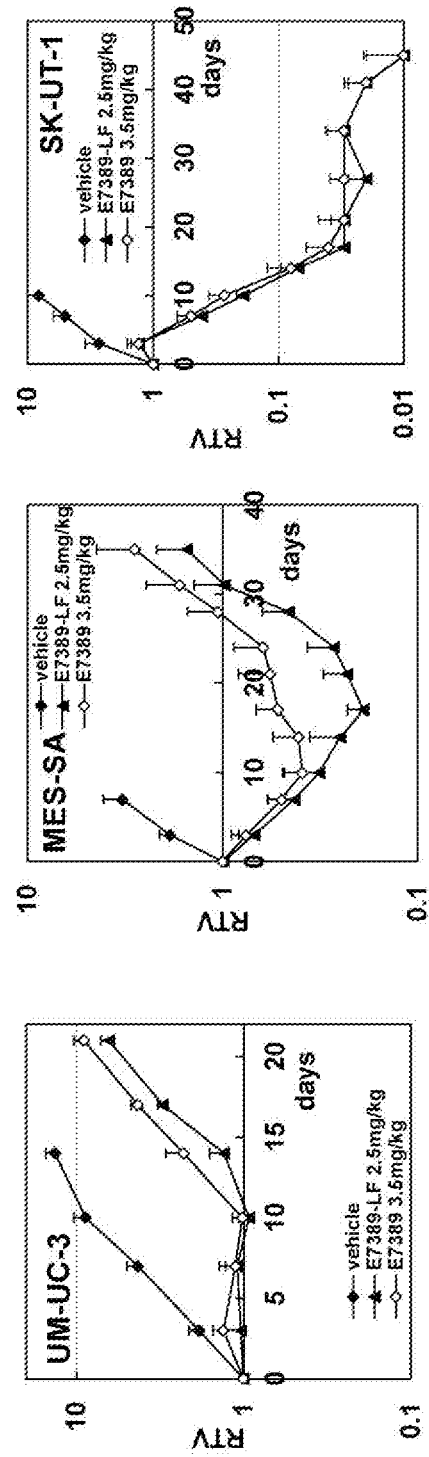
FIG. 1D shows the in vivo anti-tumor activity of a liposome composition comprising eribulin mesylate in nude mice with a different kind of tumor.

The results are given in FIG. 1A to FIG. 1D.

<Statistical Analysis>

Statistical treatment for each administration group was carried out by two-way RM-ANOVA using log RTV. A statistically significant difference was assigned when the significance probability P value was $P<0.05$ (5%). Prism6 software (Graphpad Software, Inc.) was used for the statistical analysis.

<Results>

The results of statistical analysis by RM-ANOVA using the log RTV value are given in Table 4 and Table 5 for the anti-tumor activity of E7389-LF and E7389 for each of the human tumor transplant models. In the all 18 human xenograft models, the anti-tumor activity of E7389-LF and E7389 was statistically significant compared to the vehicle group. In addition, in the 11 models, the anti-tumor activity of E7389-LF was statistically significant compared to the anti-tumor activity of E7389.

In the tables, the term "Yes 1" indicates that there is a statistically significant difference, comparing the tumor volume change with E7389-LF or E7389 to the tumor volume change in the vehicle group. The term "Yes 2" indicates that there is a statistically significant difference, comparing, the tumor volume change with E7389-LF to the tumor volume change with E7389. The term "NS" indicates that there is no statistically significant difference, comparing the tumor volume change with E7389-LF to the tumor volume change with E7389.

The term "day X" indicates the experimental period during which the RM-ANOVA testing was performed.

TABLE 4

| | | RM-ANOVA | | |
|---|---|---|---|---|
| | | E7389-LF vs vehicle | E7389 vs vehicle | E7389-LF vs E7389 |
| OMC9 | sarcoma (leiomyosarcoma) | Yes 1 day 7-day 35 | Yes 1 day 7-day 35 | NS day 7-day 49 |
| MES-SA | sarcoma (leiomyosarcoma) | Yes 1 day 4-day 18 | Yes 1 day 4-day 18 | Yes 2 day 4-day 46 |
| SK-UT-1 | sarcoma (leiomyosarcoma) | Yes 1 day 3-day 10 | Yes 1 day 3-day 10 | NS day 3-day 48 |
| SK-LMS-1 | sarcoma (leiomyosarcoma) | Yes 1 day 2-day 7 | Yes 1 day 2-day 7 | Yes 2 day 2-day 31 |
| A673 | sarcoma (Ewing sarcoma) | Yes 1 day 4-day 18 | Yes 1 day 4-day 18 | NS day 4-day 25 |
| MFE-280 | uterine cancer (endometrial cancer) | Yes 1 day 4-day 14 | Yes 1 day 4-day 14 | Yes 2 day 4-day 71 |
| MFE-296 | uterine cancer (endometrial cancer) | Yes 1 day 4-day 14 | Yes 1 day 4-day 14 | Yes 2 day 4-day 68 |
| HEC-151 | uterine cancer (endometrial cancer) | Yes 1 day 3-day 14 | Yes 1 day 3-day 14 | NS day 3-day 49 |
| ECC-1 | uterine cancer (endometrial cancer) | Yes 1 day 4-day 19 | Yes 1 day 4-day 19 | Yes 2 day 4-day 39 |
| KB (HeLa) | uterine cancer (cervical cancer) | Yes 1 day 7-day 14 | Yes 1 day 7-day 14 | Yes 2 day 7-day 21 |
| AsPC-1 | pancreatic cancer | Yes 1 day 3-day 35 | Yes 1 day 3-day 35 | Yes 2 day 3-day 35 |
| BXPC-3 | pancreatic cancer | Yes 1 day 7-day 21 | Yes 1 day 7-day 21 | Yes 2 day 7-day 49 |
| KP-1 | pancreatic cancer | Yes 1 day 3-day 14 | Yes 1 day 3-day 14 | Yes 2 day 3-day 49 |
| K1 | thyroid cancer | Yes 1 day 3-day 17 | Yes 1 day 3-day 17 | NS day 3-day 24 |
| U251MG | brain tumor (glioblastoma) | Yes 1 day 5-day 23 | Yes 1 day 5-day 23 | NS day 5-day 40 |
| PLC/PRF/5 | liver cancer (hepatocellular carcinoma) | Yes 1 day 4-day 18 | Yes 1 day 4-day 18 | NS day 4-day 56 |
| Hs746T | stomach cancer | Yes 1 day 4-day 11 | Yes 1 day 4-day 11 | Yes 2 day 4-day 63 |
| UM-UC-3 | urothelial cancer (bladder cancer) | Yes 1 day 3-day 10 | Yes 1 day 3-day 10 | NS day 3-day 21 |

TABLE 5

| | | RM-ANOVA | | |
|---|---|---|---|---|
| | | E7389-LF vs vehicle | E7389 vs vehicle | E7389-LF vs E7389 |
| MES-SA | sarcoma (leiomyosarcoma) | Yes 1 day 3-day 7 | Yes 1 day 3-day 7 | Yes 2 day 3-day 35 |
| SK-UT-1 | sarcoma (leiomyosarcoma) | Yes 1 day 3-day 10 | Yes 1 day 3-day 10 | NS day 3-day 45 |
| UM-UC-3 | urothelial cancer (bladder cancer) | Yes 1 day 3-day 14 | Yes 1 day 3-day 14 | Yes 2 day 3-day 21 |

What is claimed is:

1. A method of inhibiting growth of stomach cancer in a patient in need thereof, comprising administering to the patient a liposome composition comprising (i) eribulin or a pharmaceutically acceptable salt thereof, (ii) a phosphatidyl choline, (iii) a cholesterol, (iv) a polyethylene glycol 2000-phosphatidylethanolamine, and (vi) ammonium sulfate.

2. The method according to claim 1, wherein the eribulin or the pharmaceutically acceptable salt thereof is eribulin mesylate.

3. The method according to claim 1, wherein the phosphatidyl choline is hydrogenated soybean phosphatidylcholine (HSPC).

* * * * *